United States Patent
Gutierrez et al.

(10) Patent No.: US 12,023,102 B2
(45) Date of Patent: Jul. 2, 2024

(54) SYSTEMS AND METHODS FOR RECONSTRUCTION AND CHARACTERIZATION OF PHYSIOLOGICALLY HEALTHY AND PHYSIOLOGICALLY DEFECTIVE ANATOMICAL STRUCTURES TO FACILITATE PRE-OPERATIVE SURGICAL PLANNING

(71) Applicant: Encore Medical, LP DBA DJO Surgical, Austin, TX (US)

(72) Inventors: Sergio Gutierrez, Tampa, FL (US); Joseph P. Iannotti, Cleveland, OH (US); Mark A. Frankle, Tampa, FL (US); Gerald Williams, Philadelphia, PA (US); Thomas Brad Edwards, Houston, TX (US); Jonathan Levy, Oakland Park, FL (US); Joseph A. Abboud, Philadelphia, PA (US)

(73) Assignee: Encore Medical, LP DBA DJO Surgical, Austin, TX (US)

( * ) Notice: Subject to any disclaimer, the term of this patent is extended or adjusted under 35 U.S.C. 154(b) by 0 days.

(21) Appl. No.: 17/061,221

(22) Filed: Oct. 1, 2020

(65) Prior Publication Data
US 2021/0100618 A1 Apr. 8, 2021

Related U.S. Application Data

(60) Provisional application No. 62/909,423, filed on Oct. 2, 2019.

(51) Int. Cl.
*A61B 34/10* (2016.01)
*G06N 20/00* (2019.01)
(Continued)

(52) U.S. Cl.
CPC ............ *A61B 34/10* (2016.02); *G06N 20/00* (2019.01); *G16H 30/40* (2018.01); *G16H 50/20* (2018.01);
(Continued)

(58) Field of Classification Search
CPC ........ G16H 50/50; G16H 30/40; G16H 50/20; G16H 20/40; A61B 34/10;
(Continued)

(56) References Cited

U.S. PATENT DOCUMENTS

| 9,195,801 B1 | 11/2015 | Sankaran et al. |
| 2003/0078759 A1 * | 4/2003 | Defranoux ............. G16H 50/50 703/11 |

(Continued)

FOREIGN PATENT DOCUMENTS

| JP | 2011518645 A | 6/2011 |
| JP | 2017528181 A | 9/2017 |

(Continued)

OTHER PUBLICATIONS

Dines et al., "Novel Solution for Massive Glenoid Defects in Shoulder Arthroplasty: A Patient-Specific Glenoid Vault Reconstruction System," The American Journal of Orthopedics, Mar./Apr. 2017, pp. 104-108.

(Continued)

*Primary Examiner* — Karen A Hranek
(74) *Attorney, Agent, or Firm* — Veros Legal Solutions, LLP

(57) ABSTRACT

A pre-operative surgical planning system utilizes machine learning classification to provide candidate elements of a pre-operative surgical plan. The pre-operative surgical planning system may comprise a machine learning reconstruction engine that is trained with artificial computer models of physiologically compromised anatomical structures.

7 Claims, 19 Drawing Sheets

(51) Int. Cl.
*G16H 30/40* (2018.01)
*G16H 50/20* (2018.01)
*G16H 50/50* (2018.01)

(52) U.S. Cl.
CPC ........ *G16H 50/50* (2018.01); *A61B 2034/105* (2016.02); *A61B 2034/108* (2016.02)

(58) Field of Classification Search
CPC ........ A61B 2034/105; A61B 2034/108; A61B 34/25; A61B 2034/107
See application file for complete search history.

(56) References Cited

U.S. PATENT DOCUMENTS

| | | | |
|---|---|---|---|
| 2008/0269906 A1* | 10/2008 | Iannotti | A61F 2/30942 703/11 |
| 2009/0270868 A1 | 10/2009 | Park et al. | |
| 2012/0281900 A1* | 11/2012 | Rueckert | G06T 7/11 382/128 |
| 2014/0278322 A1* | 9/2014 | Jaramaz | G16Z 99/00 703/11 |
| 2015/0328004 A1* | 11/2015 | Mafhouz | A61F 2/2875 700/98 |
| 2016/0015465 A1* | 1/2016 | Steines | A61F 2/30942 623/18.11 |
| 2016/0331463 A1* | 11/2016 | Nötzli | A61B 34/10 |
| 2018/0263586 A1* | 9/2018 | Henchie | G16H 50/30 |
| 2019/0005186 A1* | 1/2019 | Nikou | G16H 50/20 |
| 2019/0239926 A1* | 8/2019 | Pavlovskaia | G06T 7/12 |
| 2020/0030034 A1* | 1/2020 | Kontaxis | A61F 2/3094 |
| 2020/0289050 A1* | 9/2020 | Moctezuma de la Barrera | A61B 5/7275 |
| 2020/0364864 A1* | 11/2020 | Shanbhag | G06T 7/0014 |
| 2022/0054197 A1* | 2/2022 | Plessers | G16H 30/40 |
| 2022/0148167 A1* | 5/2022 | Poltaretskyi | G06T 7/0012 |
| 2022/0202497 A1* | 6/2022 | Janna | A61F 2/30756 |
| 2022/0398817 A1* | 12/2022 | Chaoui | A61B 34/10 |
| 2023/0186495 A1* | 6/2023 | Poltaretskyi | G06T 7/55 345/630 |

FOREIGN PATENT DOCUMENTS

| | | | |
|---|---|---|---|
| WO | 2016118521 A1 | 7/2016 | |
| WO | WO-2017085478 A1 * | 5/2017 | ........ A61F 2/30942 |
| WO | 2018067966 | 4/2018 | |

OTHER PUBLICATIONS

Asma Salhi et al., "Statistical Shape Modeling Approach to Predict Missing Scapular Bone," Annals of Biomedical Engineering, Springer US, New York, vol. 48, No. 1 (Sep. 11, 2019), pp. 367-379.

Gerard A. Engh, "Classification of Bone Defects Femur and Tibia," pp. 116-132.

Grogan et al., "Evaluation of Humeral and Glenoid Bone Deformity in Glenohumeral Arthritis," Complex and Revision Shoulder Arthroplasty, pp. 3-13, ISBN 978-3-030-02755-1.

Rodriguez et al., "Pre-Operative Planning for Reverse Shoulder Replacement: The Surgical Benefits and Their Clinical Translation," Annals of Joint, 2019; vol. 4, No. 4, pp. 1-15.

* cited by examiner

SYSTEMS AND METHODS FOR RECONSTRUCTION AND CHARACTERIZATION OF PHYSIOLOGICALLY HEALTHY AND PHYSIOLOGICALLY DEFECTIVE ANATOMICAL STRUCTURES TO FACILITATE PRE-OPERATIVE SURGICAL PLANNING

RELATED APPLICATIONS

This application claims priority To U.S. Provisional Application 62/909,423, filed on Oct. 2, 2019. The entire disclosures of all the related applications set forth in this section are hereby incorporated by reference in their entireties.

BACKGROUND

Current surgical preparation techniques often involve pre-operation planning/templating where a computer model of an anatomical structure and surrounding area that will be the subject of the surgery is derived from various imaging modalities (e.g., Magnetic Resonance Imaging (MRI), Computed Tomography (CT), X-rays, etc.). A surgeon can then evaluate different strategies for different aspects of the surgery to be conducted and have a virtually pre-tested plan for execution.

In the orthopedics field, pre-operative surgical planning systems have been developed that allow a surgeon to plan an arthroplasty or other procedure by virtually placing 2D or 3D models of candidate implants into 2D or 3D images of the patient's joint or a 2D or 3D rendering of a computer model of the patient's joint. This allows the surgeon to test different positions, sizes, and types of candidate implants prior to performing the arthroplasty. It is generally advantageous to affix the implants to the bones of the joint so that the placement and orientation of the bones of the joint after surgery matches the patient's original joint as close as possible. Difficulties arise when the joint is compromised by, for example, bone loss. In this case, it is difficult to know where to place an implant because the surgeon may have no knowledge as to where the original joint line was.

Making correct decisions in a time efficient manner regarding appropriate implant selection and placement that are made by the surgeon in this situation can require many years of training and surgical experience. A need exists for improved techniques to aid the surgeon in selecting and placing implants to return the joint to its natural placement, improving outcomes and reducing the probability that revision surgery will later be required. It should be noted that this Background is not intended to be an aid in determining the scope of the claimed subject matter nor be viewed as limiting the claimed subject matter to implementations that solve any or all of the disadvantages or problems presented above. The discussion of any technology, documents, or references in this Background section should not be interpreted as an admission that the material described is prior art to any of the subject matter claimed herein.

SUMMARY

A method of making a pre-operative surgical planning system is provided, the method comprising receiving one or more computer models of physiologically healthy anatomical structures, applying a plurality of different disorder progression simulations to the one or more computer models of physiologically healthy anatomical structures to generate a plurality of computer models of physiologically defective anatomical structures exhibiting different defect types, using at least some of the plurality of computer models of physiologically defective anatomical structures and their corresponding defect types as all or part of a training set for a machine learning algorithm, and training the machine learning algorithm to receive an input computer model of a physiologically defective anatomical structure with unknown defect type, and to assign a defect type to the input computer model.

The anatomical structures may be any portion of an organism. In some embodiments, the anatomical structures comprise various joints, such as shoulder joints. In this case, each of the one or more computer models of physiologically healthy anatomical structures may have a glenohumeral alignment line as an anatomical characteristic thereof. The one or more computer models of physiologically healthy anatomical structures may comprise either or both replicating computer models and/or artificial computer models. The computer models of the training set may comprise either or both replicating computer models and/or artificial computer models.

Also provided are pre-operative surgical planning systems made with any one of the above methods.

Also provided are methods of pre-operative planning for a surgical procedure to be performed on a physiologically defective anatomical structure of a patient and the surgical procedures performed according to pre-operative surgical plans.

A method of pre-operative planning for a surgical procedure to be performed on a physiologically defective anatomical structure of a patient, may comprise generating or receiving, with a computerized pre-operative surgical planning system, a computer model of the patient's physiologically defective anatomical structure, based at least in part on the computer model of the patient's physiologically defective anatomical structure, generating or selecting with the computerized pre-operative surgical planning system at least one anatomical structure and/or anatomical characteristic that approximates the patient's anatomical structure and/or anatomical characteristic prior to the patient's anatomical structure becoming defective, and displaying a visual representation of the at least one anatomical structure and/or anatomical characteristic that approximates the patient's anatomical structure and/or anatomical characteristic prior to the patient's anatomical structure becoming defective. The generating or selecting at least one anatomical structure and/or anatomical characteristic that approximates the patient's anatomical structure and/or anatomical characteristic prior to the patient's anatomical structure becoming compromised may be performed using a machine learning classifier.

This method may further include generating, with the computerized pre-operative surgical planning system, at least one candidate element for a pre-operative surgical plan based at least in part on the generated or selected anatomical structure and/or anatomical characteristic that approximates the patient's anatomical structure and/or anatomical characteristic prior to the patient's anatomical structure becoming defective, and displaying a visual representation of the generated candidate element of the pre-operative surgical procedure plan.

This method may identify a defect type exhibited by the physiologically defective anatomical structure of the patient. Identifying the defect type may be performed by a machine learning classifier.

The generated candidate element of the pre-operative surgical procedure plan may comprise a selection of an implant to be affixed to the patient's compromised anatomical structure during the surgical procedure.

A method may comprise generating or receiving, with a computerized pre-operative surgical planning system, a computer model of the patient's physiologically defective anatomical structure, with the computerized pre-operative surgical planning system, assigning a defect type from a set of pre-defined defect types to the patient's physiologically defective anatomical structure based at least in part on the generated or received computer model of the patient's physiologically defective anatomical structure, wherein each defect type of the set of pre-defined defect types corresponds to a pre-defined disorder progression simulation algorithm.

This method may comprise generating, with the computerized pre-operative surgical planning system, at least one candidate element for a pre-operative surgical plan based at least in part on the assigned defect type, and displaying a visual representation of the generated candidate element of the pre-operative surgical procedure plan.

The generated candidate element of the pre-operative surgical plan comprises a selection of an implant to be affixed to the patient's compromised anatomical structure during the surgical procedure.

The method may comprise generating or selecting with the computerized pre-operative surgical planning system at least one computer model of an anatomical structure and/or anatomical characteristic that approximates the patient's anatomical structure and/or anatomical characteristic prior to the patient's anatomical structure becoming defective based at least on part on the assigned defect type and visually displaying the computer model of the at least one anatomical structure and/or anatomical characteristic that approximates the patient's anatomical structure and/or anatomical characteristic prior to the patient's anatomical structure becoming defective. The method may also include visually displaying the computer model of the patient's physiologically defective anatomical structure.

The method may comprise visually displaying the computer model of the at least one anatomical structure and/or anatomical characteristic that approximates the patient's anatomical structure and/or anatomical characteristic prior to the patient's anatomical structure becoming defective overlaid on the computer model of the patient's physiologically defective anatomical structure.

The method may comprise visually displaying candidate implants overlaid on either or both of the computer model of the at least one anatomical structure and/or anatomical characteristic that approximates the patient's anatomical structure and/or anatomical characteristic prior to the patient's anatomical structure becoming compromised and the computer model of the patient's compromised anatomical structure.

A method of performing a surgical procedure on a physiologically defective anatomical structure of a patient may comprise generating or receiving, with a computerized pre-operative surgical planning system, a computer model of the patient's physiologically defective anatomical structure, with the computerized pre-operative surgical planning system, assigning a defect type from a set of pre-defined defect types to the patient's physiologically defective anatomical structure based at least in part on the generated or received computer model of the patient's physiologically defective anatomical structure, wherein each defect type of the set of pre-defined defect types corresponds to a pre-defined disorder progression simulation algorithm, generating, with the computerized pre-operative surgical planning system, at least one candidate element for a pre-operative surgical procedure plan based at least in part on the assigned defect type, providing user input to the computerized pre-operative surgical planning system for modifying and/or supplementing the at least one generated candidate element for the pre-operative surgical procedure plan, and performing the surgical procedure based at least in part on the generated candidate element as modified and/or supplemented by the user input.

The surgical procedure may comprise affixing an implant to the patient's physiologically defective anatomical structure.

The method may comprise selecting a candidate implant for the pre-operative surgical procedure plan based at least in part on the assigned defect type. This selection may be done automatically by the pre-operative surgical planning system in response to the assigned defect type.

The method may include displaying the candidate implant together with the computer model of the patient's defective anatomical structure.

Assigning the defect type may be performed using a trained machine learning algorithm. In this embodiment, the trained machine learning algorithm may be trained with a training set comprising artificial computer models of anatomical structures generated by one or more disorder progression simulations.

Also provided are pre-operative surgical planning systems. Such systems may comprise memory configured to store a computer model of the physiologically compromised anatomical structure of the patient, and may further comprise processing circuitry configured to assign a defect type from a set of pre-defined defect types to the patient's physiologically defective anatomical structure based at least in part on the stored computer model of the patient's physiologically defective anatomical structure, wherein each defect type of the set of pre-defined defect types corresponds to a pre-defined disorder progression simulation algorithm.

The processing circuitry may be configured to execute a trained machine learning algorithm to assign the defect type.

The processing circuitry may be configured to generate or select at least one computer model of an anatomical structure and/or anatomical characteristic that approximates the patient's anatomical structure and/or anatomical characteristic before becoming defective, wherein the generating and selecting is based at least in part on the assigned defect type.

The system may further comprise a display configured to present the generated or selected at least one computer model of an anatomical structure and/or anatomical characteristic that approximates the patient's anatomical structure and/or anatomical characteristic before becoming defective.

Any of the above systems may be used to execute all or part of any of the described pre-operative surgical planning methods set forth above.

It is understood that various configurations of the subject technology will become apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

Various embodiments are discussed in detail in conjunction with the Figures described below, with an emphasis on highlighting the advantageous features. These embodiments are for illustrative purposes only and any scale that may be illustrated therein does not limit the scope of the technology disclosed. These drawings include the following figures, in which like numerals indicate like parts.

DETAILED DESCRIPTION

Figure 1:
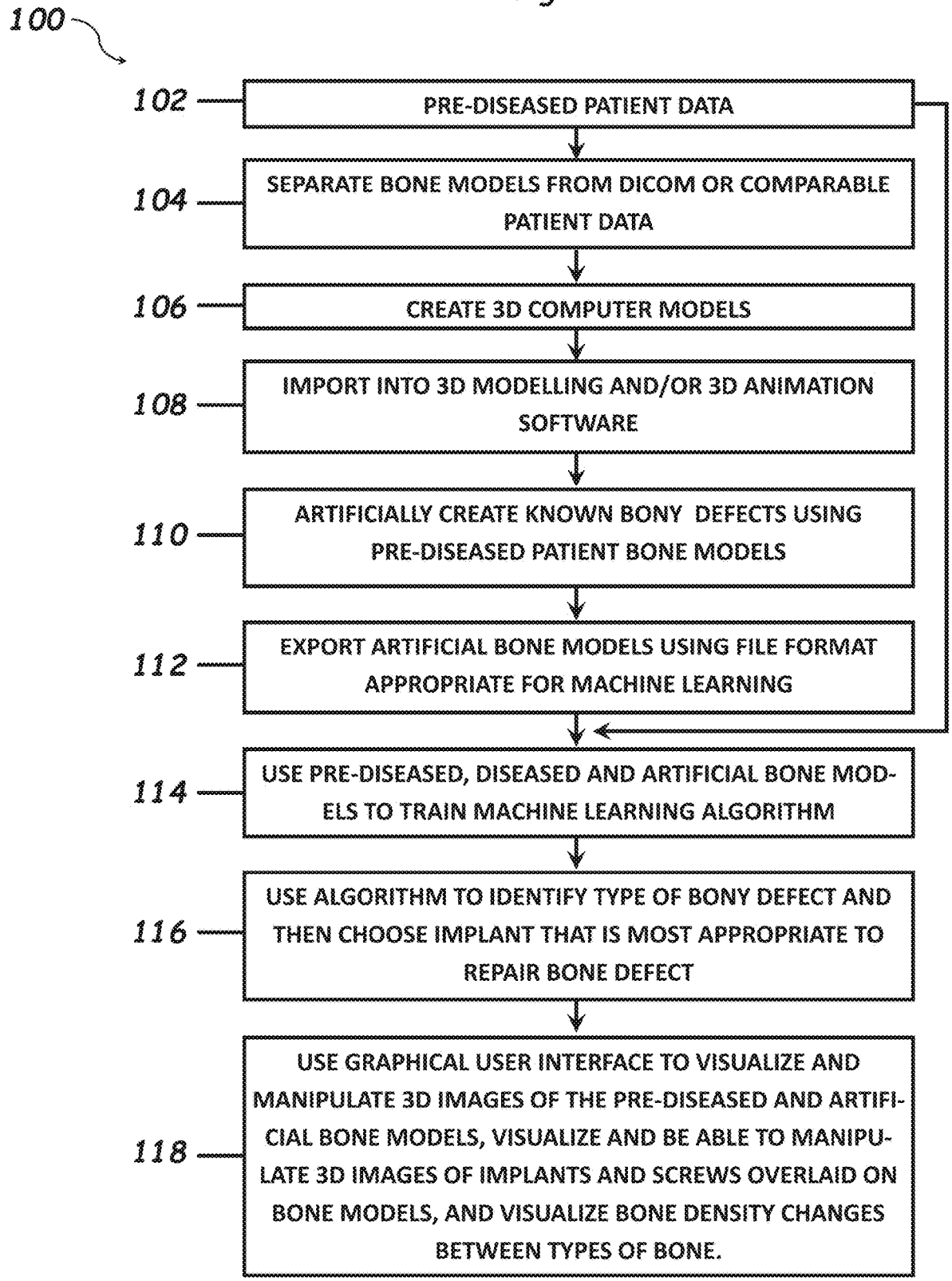
FIG. 1 is a flow chart for a method for modifying a bone for use in a machine learning algorithm in accordance with a first embodiment of the present invention.

The following description and examples illustrate some exemplary implementations, embodiments, and arrangements of the disclosed invention in detail. Those of skill in the art will recognize that there are numerous variations and modifications of this invention that are encompassed by its scope. Accordingly, the description of a certain example embodiment should not be deemed to limit the scope of the present invention.

Implementations of the technology described herein are directed generally to methods and systems for surgical planning incorporating machine learning algorithms and the development of the machine learning algorithms themselves. The systems, methods, and components described and illustrated herein can be used to treat any anatomical structure within the body of an animal, including, but not limited to, humans. Skilled artisans will be able to select a suitable anatomical structure within the body of an animal to utilize a system and/or method described herein according to a particular embodiment based on various considerations, including the type of ailment and/or the structural arrangement at a treatment site.

Orthopedics, especially joint arthroplasty, may utilize the systems and methods described herein. Example joints considered suitable to utilize a system, method, and/or component described herein include, but are not limited to, the shoulder joint, the elbow joint, the knee joint, the hip joint, and the ankle joint.

According to an exemplary embodiment of the present invention, normal, healthy, or pre-diseased patient data (e.g., Digital Imaging and Communications in Medicine (DICOM) or comparable format) is used to generate at least one 3D model of a physiologically healthy joint, where the joint consists of 2 or more bones. Using 3D modelling software, the first bone of the physiologically healthy joint is used to artificially create a predefined bony defect on the second bone. The predefined defects can be created according to predetermined disorder progression simulation parameters that are based on a mathematical coordinate system and its related planes and known properties of physiological defect creation in a given anatomical structure. The planes of the mathematical coordinate system can be aligned to the planes of an anatomical coordinate system (i.e., axial, coronal and sagittal planes) if so desired. The predetermined parameters can include: 1) distance of the first bone in relation to the second bone by using landmarks internal to or on the surface of both bones for the desired distance or by using a landmark that is external to the bones or 2) angle of the first bone in relation to the second bone by using landmarks internal to or on the surface of both bones for the desired distance or by using a landmark that is external to the bones. The defects created in the second bone by the first bone can be of the following types: 1) Boolean—a subtractive removal of bone or 2) displacement—moving of bone model in multiple different directions according to the shape of the bone creating the defect, e.g. colliding one bone into another. Multiple different defect types can be created using different defect creation parameters to produce a set of artificial computer models of physiologically defective joints having different defect types. A particular set of disorder progression parameters corresponds to a particular defect type. The at least one physiologically healthy 3D model and the artificially created 3D models may be used for training purposes in a machine learning algorithm. Additionally, a patient's contralateral side CT can be used to train a machine learning algorithm to identify defect types present in new patients and re-create approximations of the currently defective joints of new patients when they were physiologically healthy. This information can be used to improve the pre-operative surgical planning process, especially for physicians that do not have extensive experience in orthopedic surgery. For example, the trained machine learning algorithm can be used for the following:

(1) identify the type of bone defect exhibited by a new patient and then choose an implant from a repository of implants that is predicted to place the bones of the joint in a position that best matches predicted healthy bone locations (2) identify the best position for an implant and/or screws based on the type of bone (cortical or cancellous) present and the quality (density) of bone present in a joint exhibiting a particular defect type (3) identify the type of bone defect exhibited by a new patient and then select a healthy bone model from a library of bone models that the algorithm predicts is most similar to the patient's original healthy joint (4) identify the type of bone defect and then recreate missing bone of the patient's joint based on the healthy joint models it used for training (5) identify the type of bone defect and then recreate missing bone of the patient's joint based on the patient's current contralateral side CT by, for example, reversing the disorder progression algorithm that will create the identified defect with the computer model of the patient's physiologically defective joint as a starting point.

To facilitate an understanding of the various embodiments described herein, certain terms are explicitly defined below.

DEFINITIONS

Computer model: Digital data defining positions, orientations, and/or other attributes of a physical structure or object and/or the components thereof. A computer model may be stored in an electronic memory of a computer or computing system and may be visually displayable to a user of a computer system on a graphical user interface such as a display with image rendering software. A computer model may be 1-dimensional, 2-dimensional, or 3-dimensional. Computer aided design and modeling software can allow a user to manipulate a 3D visualization to view different portions, sides, or viewing angles of the represented physical structure or object.

Replicating Computer Model: A computer model that is a substantially accurate representation of a specific physical structure or object. A replicating computer model is generally based on physical measurements, images, or other information that is or was acquired directly from the specific physical structure or object that is intended to be represented by the model.

Artificial Computer Model: A computer model that represents a notional structure or object. The notional structure or object represented by an artificial computer model may, for example, be a representation of a modified version of specific physical structure or object, may include attributes found separately in a plurality of different physical structures or objects, may include attributes that are averages of shapes, dimensions, or other attributes of a plurality of different specific physical structures or objects, or may represent a prediction or approximation of attributes of a single physical structure or object for which sufficient measurements, images, or other information from which a replicating computer model could be created are unavailable.

Anatomical Structure: A defined portion of an organism that may be subjected to a surgical procedure. Usually, but not necessarily, an anatomical structure will be a defined functional component of the organism or a related set of functional components of the organism such as an organ, an extremity, a bone, a joint, or the like.

Anatomical Characteristic: A physical attribute or property of an anatomical structure or one or more of the components thereof. Anatomical characteristics include but are not limited to volume, orientation, position, alignment axis, shape, and the like.

Pre-operative Surgical Planning: Defining an action, a series of actions, an order of actions, a tool selection, an implant selection, or any other element or set of elements of a surgical procedure prior to performing the surgical procedure.

Pre-operative Surgical Plan: The combined elements of a surgical procedure that are defined during pre-operative surgical procedure planning. A pre-operative surgical procedure plan may define only one, only some, or essentially all elements of a complete surgical procedure.

Pre-operative Surgical Planning System: A computer system storing information related to an anatomical structure that may be the subject of a surgical procedure together with a user interface that allows a surgeon to visualize at least some aspects of the anatomical structure, surgical tools, implants to be affixed, and the like to test and/or predict the results of different approaches to the surgical procedure that will be performed. A pre-operative surgical planning system can semi-automate the development of a pre-operative surgical plan.

Processor: A processor is an electronic circuit configured to retrieve instructions from a memory and execute one or more arithmetic, logic, data storage, and/or data output operations defined by each instruction. A processor may execute these operations sequentially or concurrently. The term software refers to the instructions stored in the memory and retrieved by the processor. A processor may be any conventional general-purpose single- or multi-chip processor found in consumer devices such as personal computers, laptop computers, smartphones, and the like. In addition, a processor may be any conventional special purpose processor such as a digital signal processor, a graphics processor, or a microcontroller. Software may be written in a variety of programming languages such as but not limited to the various versions of C or JavaScript. Software may be stored in compiled or uncompiled form.

Software and Program: The term software or program refers to instructions stored in a memory in machine-readable form, human-readable form, or both that are executable by a processor when compiled into a machine-readable form. Software may be written in a variety of programming languages such as but not limited to the various versions of C and JavaScript. Depending on the environment of use, software may be also called firmware.

Algorithm: A connected sequence of two or more data processing acts. Software programs are implementations of algorithms.

Determining: Calculating, computing, processing, deriving, investigating, looking up (e.g., looking up in a table, a database or another data structure), ascertaining and the like. Determining may also include receiving (e.g., receiving information), accessing (e.g., accessing data in a memory) and the like. Determining may also include resolving, selecting, choosing, calculating, deriving, establishing and the like. Determining may also include ascertaining that a parameter matches a predetermined criterion, including that a threshold has been met, passed, exceeded, and so on.

Substantially: A sufficient amount or degree of a specified property that largely but not necessarily wholly provides one or more desired functions of the specified property in the context in which it is being used.

DESCRIPTION

FIG. 1 describes the first embodiment of the present invention as a method for creation of a machine learning algorithm based on pre-diseased bone models and custom models of a bone with a defect 100. The method 100 includes a first step 102 that describes starting with pre-diseased patient data, such as Digital Imaging and Communications in Medicine (DICOM) data. The method 100 further includes a second step 104 that describes separating the desired bone models from the DICOM or other comparable patient data. The method 100 further includes a third step 106 that describes creating 3D computer models from the patient data. The method 100 further includes a fourth step 108 that describes importing 3D computer models into 3d modelling and/or 3D animation software. The method 100 further includes a fifth step 110 that describes artificially creating known bone defects using pre-diseased patient bone models. The method 100 further includes a sixth step 112 that describes exporting artificially created bone models using a file format that is appropriate for machine learning. The method 100 further includes a seventh step 114 that describes using both pre-diseased, diseased and the artificially created bone models to train a machine learning algorithm to identify any differences between the pre-diseased, diseased and artificially created bone models.

A wide variety of machine learning and training techniques and strategies may be used. For example, a feature set can be extracted from the models which produces clustering of defect types in a multi-dimensional feature space. A nearest neighbor approach can then be applied to assign an input computer model with unknown defect type to a particular cluster in the feature space, thereby identifying or assigning a defect type to the input computer model.

The method 100 further includes an eighth step 116 that describes how the trained machine learning algorithm identifies the type of bone defect present in the bone model and then chooses an implant from multiple different options that would repair the bone defect. The method 100 further includes a ninth step 118 that describes using a graphical user interface (GUI) to visualize and be able to manipulate the 3D images of the pre-diseased and artificial bone models, visualize and be able to manipulate 3D images of implants and screws that are overlaid onto the 3D images of the bone models, and visualize differences in bone mineral density between different types of bone (e.g. cortical, trabecular, etc.).

Figure 2:
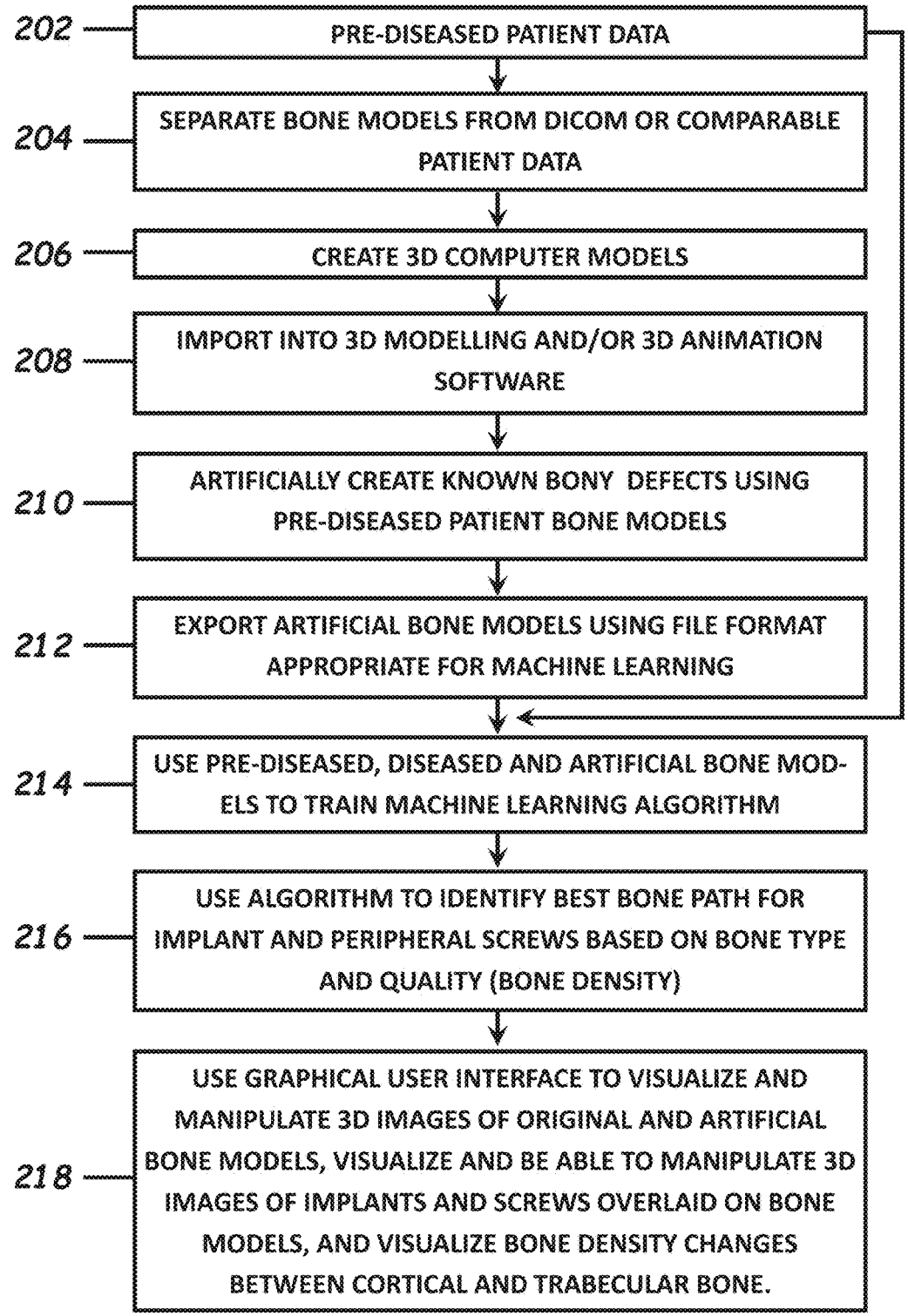
FIG. 2 is a flow chart for a method for modifying a bone for use in a machine learning algorithm in accordance with a second embodiment of the present invention.

FIG. 2 describes the first embodiment of the present invention as a method for creation of a machine learning algorithm based on pre-diseased bone models and custom models of a bone with a defect 200. The method 200 includes a first step 202 that describes starting with pre-diseased patient data, such as Digital Imaging and Communications in Medicine (DICOM) data. The method 200 further includes a second step 204 that describes separating the desired bone models from the DICOM or other comparable patient data. The method 200 further includes a third step 206 that describes creating 3D computer models from the patient data. The method 200 further includes a fourth step 208 that describes importing 3D computer models into 3d modelling and/or 3D animation software. The method 200 further includes a fifth step 210 that describes artificially creating known bone defects using pre-diseased patient bone models. The method 200 further includes a sixth step 212 that describes exporting artificially created bone models using a file format that is appropriate for machine learning. The method 200 further includes a seventh step 214 that describes using both pre-diseased, diseased and the artificially created bone models to train a machine learning algorithm to identify any differences between the pre-diseased, diseased and artificially created bone models. The method 200 further includes an eighth step 216 that describes how the trained machine learning algorithm identifies the best position on the bone model for the implant and the best path for the bone screws based on the bone type and density. The method 100 further includes a ninth step 218 that describes using a graphical user interface (GUI) to visualize and be able to manipulate the 3D images of the pre-diseased and artificial bone models, visualize and be able to manipulate 3D images of implants and screws that are overlaid onto the 3D images of the bone models, and visualize differences in bone mineral density between different types of bone (e.g., cortical, trabecular, etc.).

Figure 3:
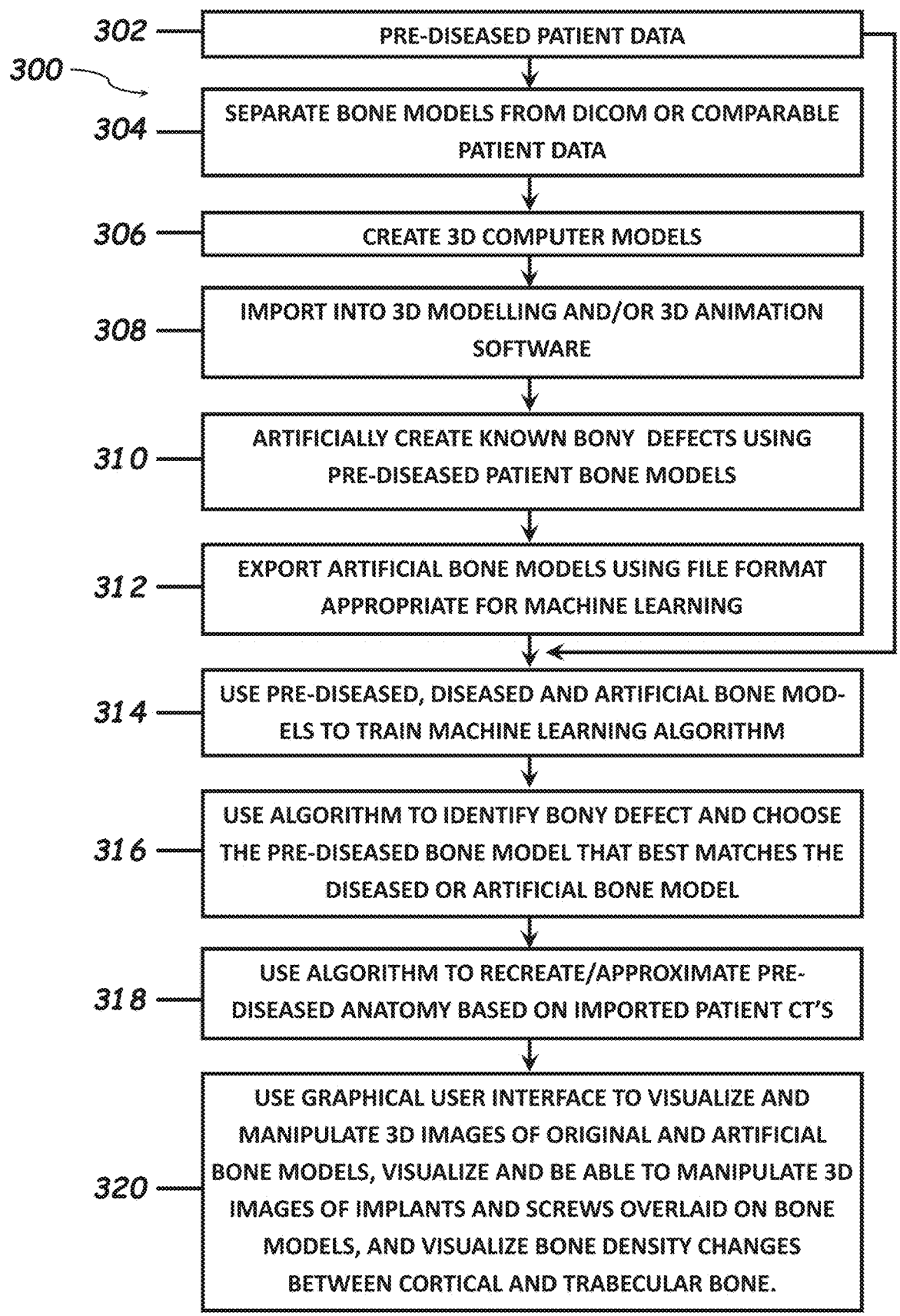
FIG. 3 is a flow chart for a method for modifying a bone for use in a machine learning algorithm in accordance with a third embodiment of the present invention.

FIG. 3 describes the first embodiment of the present invention as a method for creation of a machine learning algorithm based on pre-diseased bone models and custom models of a bone with a defect 300. The method 300 includes a first step 302 that describes starting with pre-diseased patient data, such as Digital Imaging and Communications in Medicine (DICOM) data. The method 300 further includes a second step 304 that describes separating the desired bone models from the DICOM or other comparable patient data. The method 300 further includes a third step 306 that describes creating 3D computer models from the patient data. The method 300 further includes a fourth step 308 that describes importing 3D computer models into 3d modelling and/or 3D animation software. The method 300 further includes a fifth step 310 that describes artificially creating known bone defects using pre-diseased patient bone models. The method 300 further includes a sixth step 312 that describes exporting artificially created bone models using a file format that is appropriate for machine learning. The method 100 further includes a seventh step 314 that describes using both pre-diseased, diseased and the artificially created bone models to train a machine learning algorithm to identify any differences between the pre-diseased, diseased and artificially created bone models. The method 300 further includes an eighth step 316 that describes how the trained machine learning algorithm identifies the type of bone defect present in the bone model and then chooses the pre-diseased bone model that most closely matches the diseased or artificially created bone model. The method 300 further includes a ninth step 318 that describes how the trained machine learning algorithm recreates or approximates pre-diseased anatomy based on imported patient bone model data. The method 300 further includes a tenth step 320 that describes using a graphical user interface (GUI) to visualize and be able to manipulate the 3D images of the pre-diseased and artificial bone models, visualize and be able to manipulate 3D images of implants and screws that are overlaid onto the 3D images of the bone models, and visualize differences in bone mineral density between different types of bone (e.g., cortical, trabecular, etc.).

Figure 4:
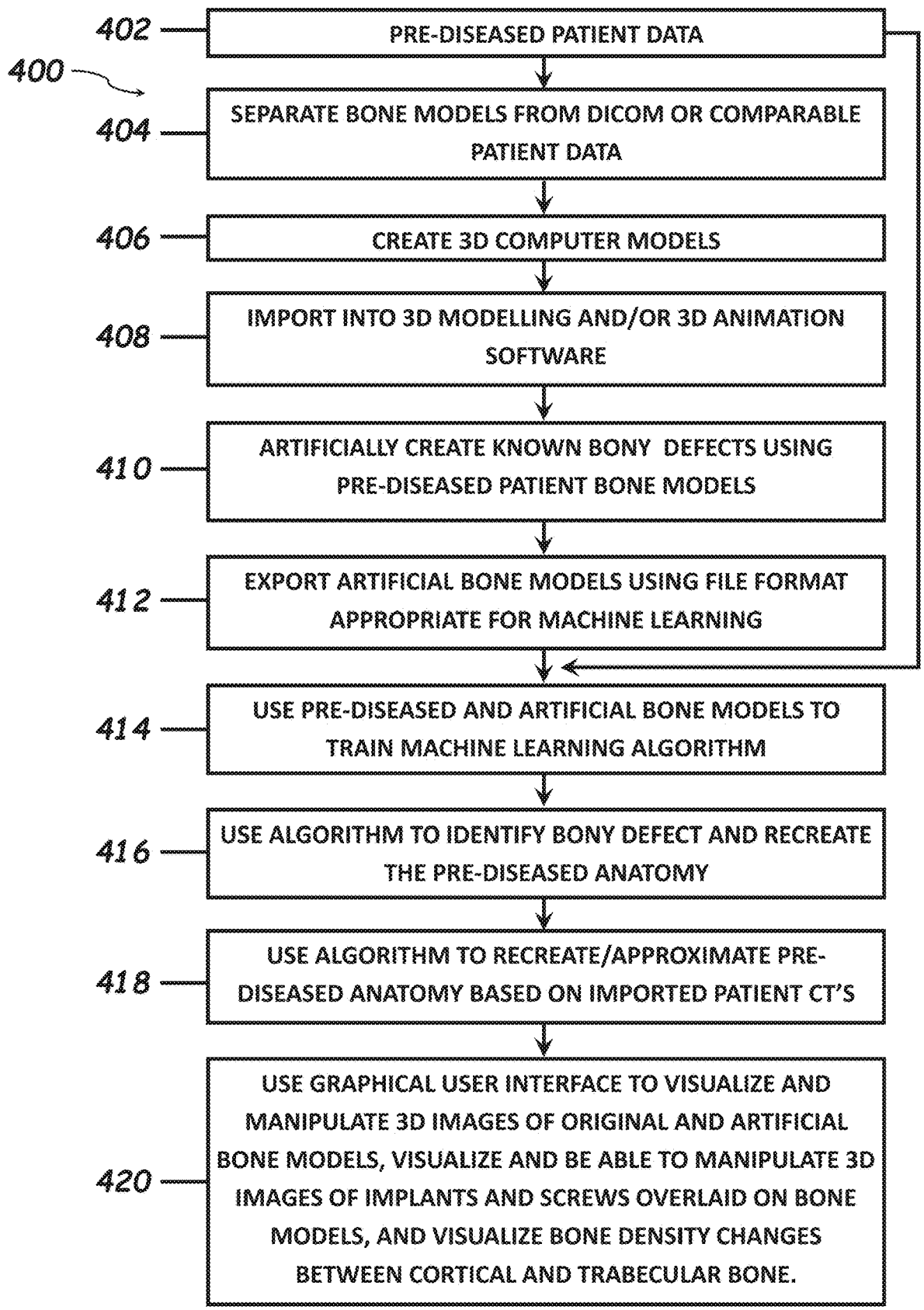
FIG. 4 is a flow chart for a method for modifying a bone for use in a machine learning algorithm in accordance with a fourth embodiment of the present invention.

FIG. 4 describes the first embodiment of the present invention as a method for creation of a machine learning algorithm based on pre-diseased bone models and custom models of a bone with a defect 400. The method 400 includes a first step 402 that describes starting with pre-diseased patient data, such as Digital Imaging and Communications in Medicine (DICOM) data. The method 400 further includes a second step 404 that describes separating the desired bone models from the DICOM or other comparable patient data. The method 400 further includes a third step 406 that describes creating 3D computer models from the patient data. The method 400 further includes a fourth step 408 that describes importing 3D computer models into 3d modelling and/or 3D animation software. The method 400 further includes a fifth step 410 that describes artificially creating known bone defects using pre-diseased patient bone models. The method 400 further includes a sixth step 412 that describes exporting artificially created bone models using a file format that is appropriate for machine learning. The method 400 further includes a seventh step 414 that describes using both pre-diseased, diseased and the artificially created bone models to train a machine learning algorithm to identify any differences between the pre-diseased, diseased and artificially created bone models. The method 400 further includes an eighth step 416 that describes how the trained machine learning algorithm identifies the type of bone defect present in the bone model and then recreates the pre-diseased anatomy. The method 400 further includes a ninth step 418 that describes how the trained machine learning algorithm recreates or approximates pre-diseased anatomy based on imported patient bone model data. The method 400 further includes a tenth step 420 that describes using a graphical user interface (GUI) to visualize and be able to manipulate the 3D images of the pre-diseased and artificial bone models, visualize and be able to manipulate 3D images of implants and screws that are overlaid onto the 3D images of the bone models, and visualize differences in bone mineral density between different types of bone (e.g., cortical, trabecular, etc.).

Figure 5:
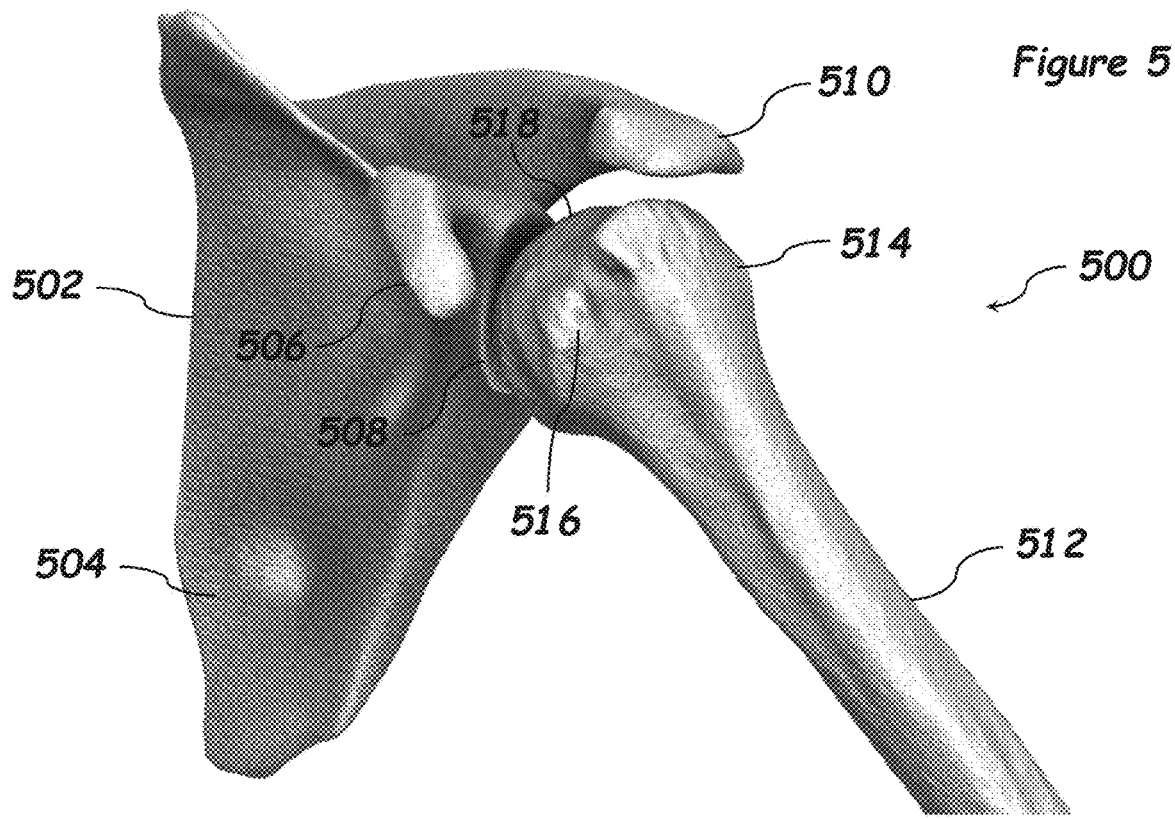
FIG. 5 is an anterior-lateral view of a shoulder that includes the scapula and humerus.

FIG. 5 illustrates an anterior-lateral shoulder view 500 that includes a scapula bone model 502 and a humerus bone model 512. The scapula bone model 502 includes an anterior portion 504, a coracoid 506, a glenoid 508 and an acromion 510. The humerus bone model 512 includes a greater tuberosity 514, a lesser tuberosity 516 and a humeral head 518.

Figure 6:
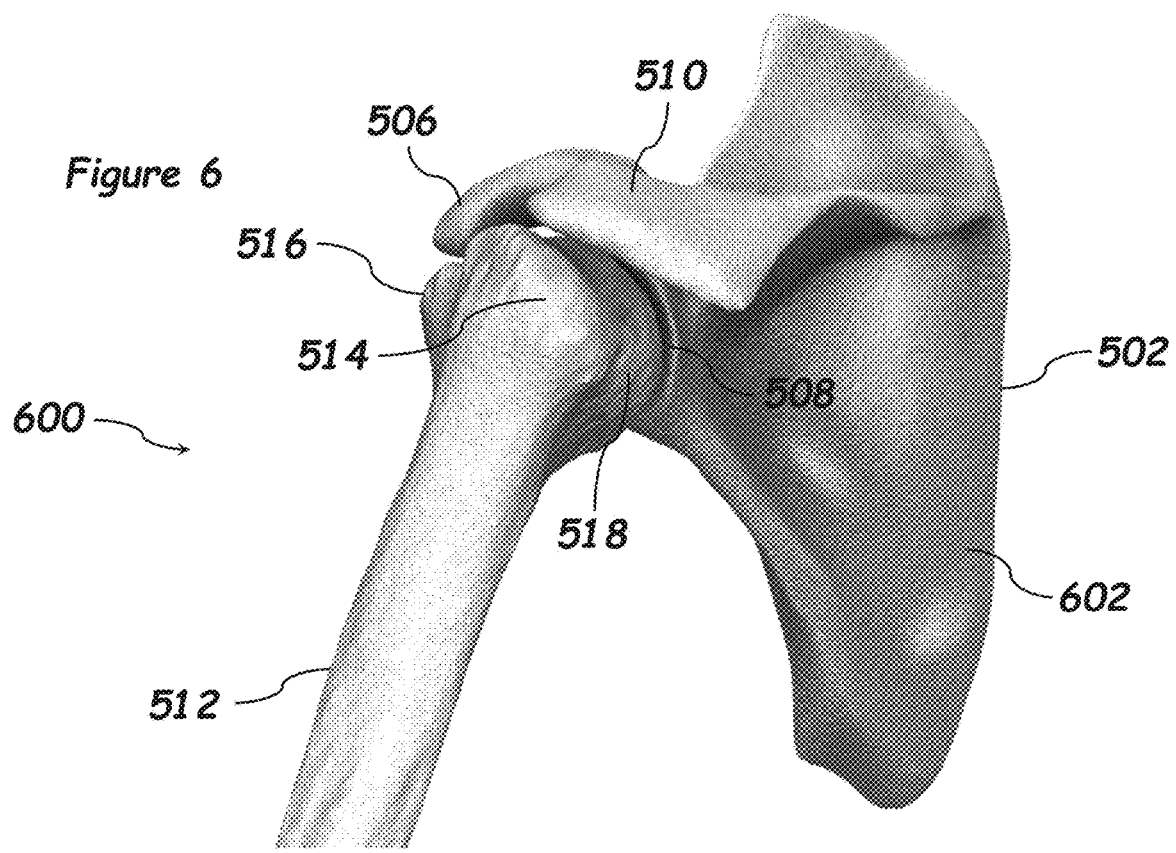
FIG. 6 is a posterior-lateral view of a shoulder that includes the scapula and humerus.

FIG. 6 illustrates a posterior-lateral shoulder view 500 that includes a scapula bone model 502 and a humerus bone model 512. The scapula bone model 502 includes a posterior portion 602, a coracoid 506, a glenoid 508 and an acromion 510. The humerus bone model 512 includes a greater tuberosity 514, a lesser tuberosity 516 and a humeral head 518.

Figure 7:
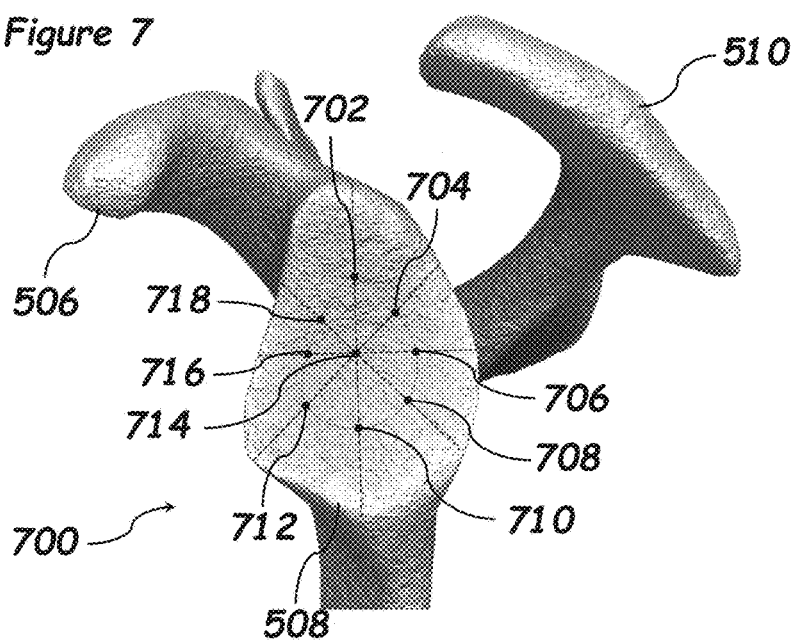
FIG. 7 is a lateral view of a scapula showing a closeup of the glenoid.

FIG. 7 illustrates a lateral scapula view 700 that includes a coracoid 506, a glenoid 508 and an acromion 510. The glenoid 508 has points 702-718 that illustrates different humerus positions to create the different bone defects required for the machine learning algorithm. Position that are available can include superior 702, superior-posterior 704, posterior 706, inferior-posterior 708, inferior 710, inferior-anterior 712, central 714, anterior 716 and superior-anterior 718.

Figure 8:
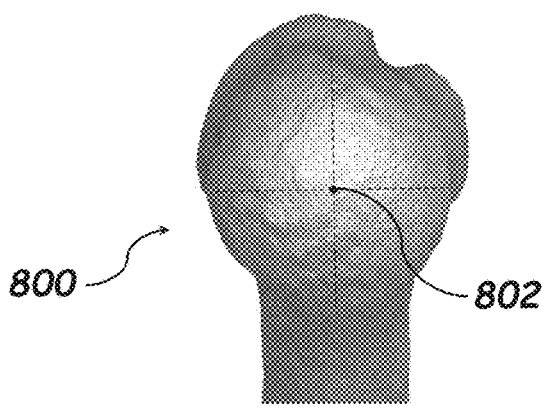
FIG. 8 is a medial view of a humerus showing a closeup of the humeral head.

FIG. 8 illustrates a medial humerus view 800 that includes a point 802 that identifies the center of the humeral head that is used to create the defects on the glenoid 508 from FIG. 7.

Figure 9:
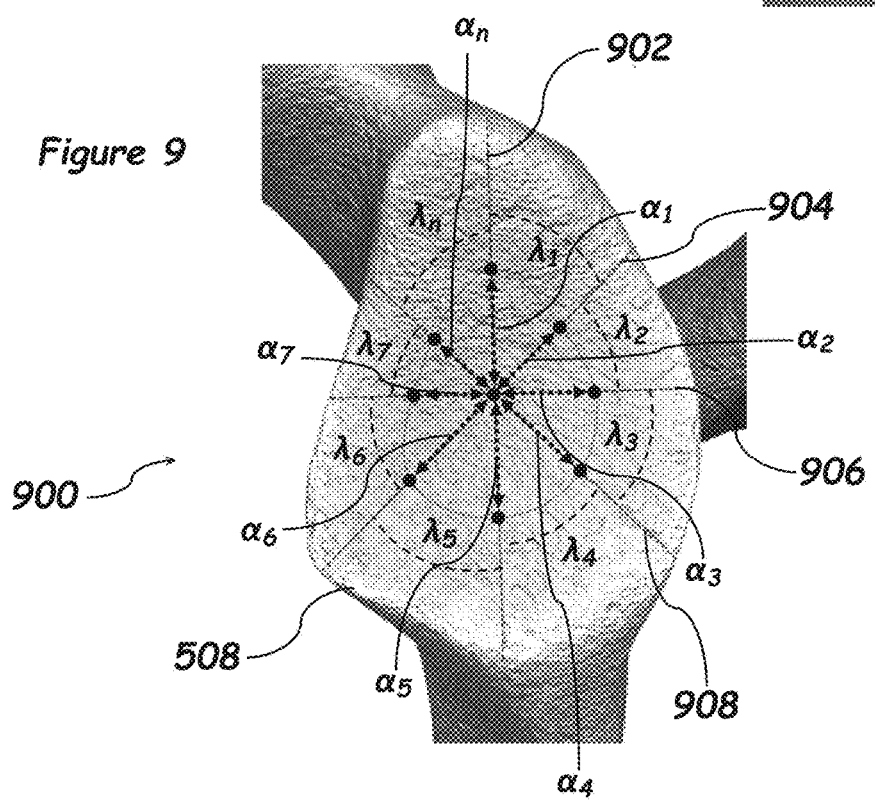
FIG. 9 is a closeup view of the glenoid showing possible placements for indent by the humerus.

FIG. 9 illustrates a closeup of the glenoid 508 and some of the variables available for the different humeral positions. The points can follow the superior/inferior axis 902, superior-posterior/inferior-anterior axis 904, anterior/posterior axis 906, and superior-anterior/inferior-posterior axis 908. Points that lie on the axis can be a distance $\alpha_1$, $\alpha_2$, $\alpha_3$, $\alpha_4$, $\alpha_5$, $\alpha_6$, $\alpha_7$, ..., an away from the center of the glenoid. Axes 902, 904, 906 and 908 can be at an angle of $\lambda_1$, $\lambda_2$, $\lambda_3$, $\lambda_4$, $\lambda_5$, $\lambda_6$, $\lambda_7$, ..., $\lambda_n$ from each other.

Figure 10:
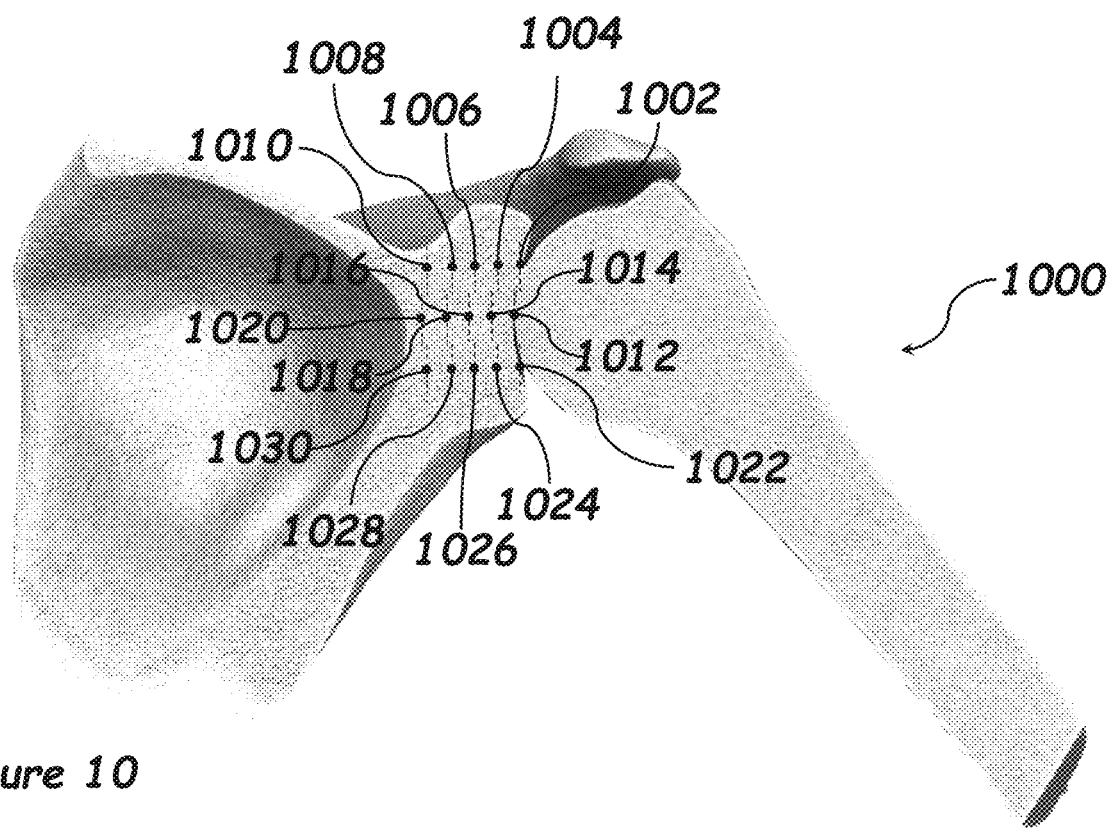
FIG. 10 is a cross-sectional view of the shoulder showing possible placements for humeral indentation.

FIG. 10 illustrates an anterior section view 1000 of the scapula and humerus. The points represent positions away from the glenoid surface, where positions 1002, 1004, 1006, 1008 and 1010 are along the superior portion of the glenoid, positions 1012, 1014, 1016, 1018 and 1020 are along the middle portion of the glenoid and positions 1022, 1024, 1026, 1028 and 1030 are along the inferior portion of the glenoid.

Figure 11:
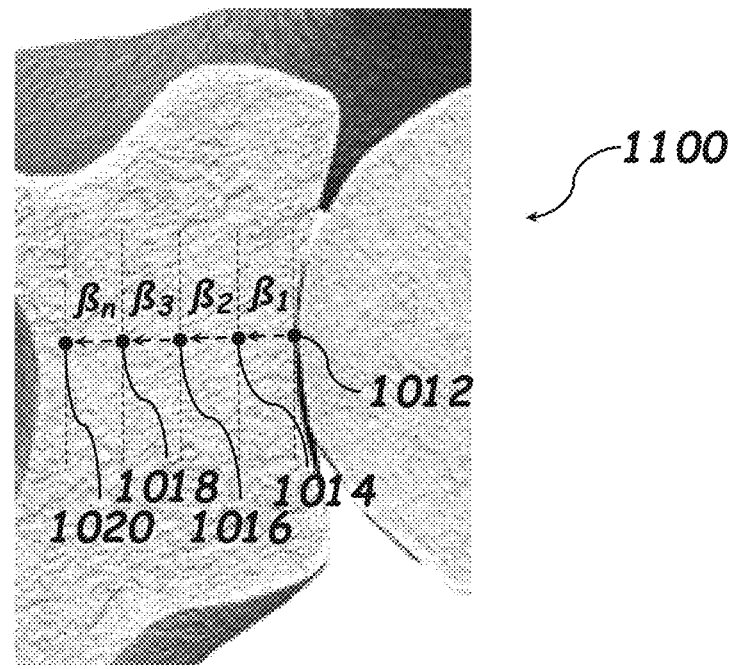
FIG. 11 is a closeup view of FIG. 10 showing possible distances for humeral indent.

FIG. 11 illustrates a closeup view 1100 of the glenoid in FIG. 10. As an illustration, the middle positions 1012, 1014, 1016, 1018 and 1020 can be a distance $\beta_1$, $\beta_2$, $\beta_3$, ..., $\beta_n$ away from the point 1012 that lies on the surface of the glenoid.

Figure 12:
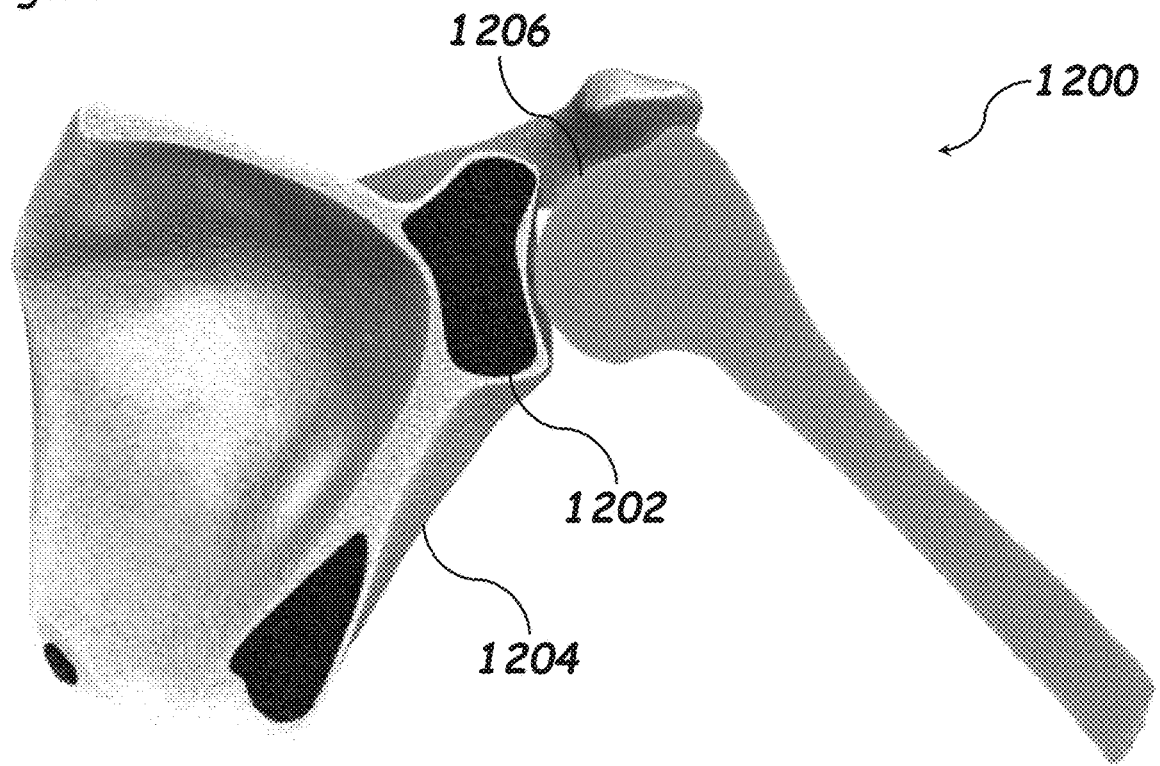
FIG. 12 is a cross-sectional view of the shoulder showing the different bone types in the scapula.

FIG. 12 illustrates an anterior section view 1200 of the scapula and humerus showing a section view of the humerus 1206, and a section view of the scapula showing the cortical bone 1204 and the trabecular bone 1202.

Figure 13:
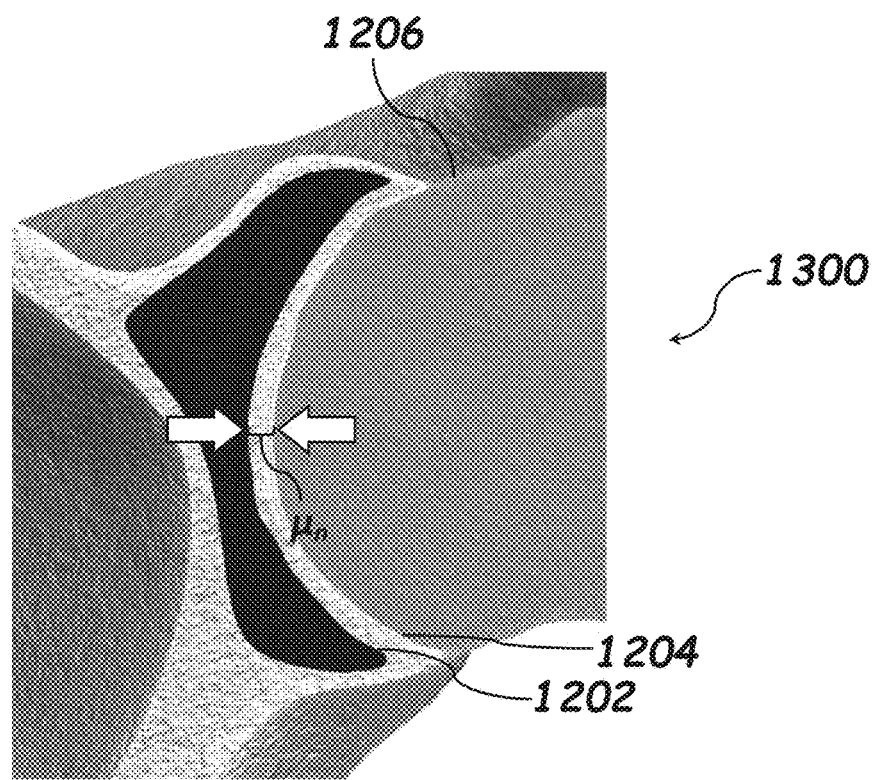
FIG. 13 is a cross-sectional view of the glenoid showing the possible changes in thickness of the cortical bone during humeral indentation.

FIG. 13 illustrates a closeup view 1300 of the glenoid in FIG. 12. The humerus 1206 can create a defect into the cortical bone 1204 an added distance $\mu_n$ from the trabecular bone 1202.

Figure 14:
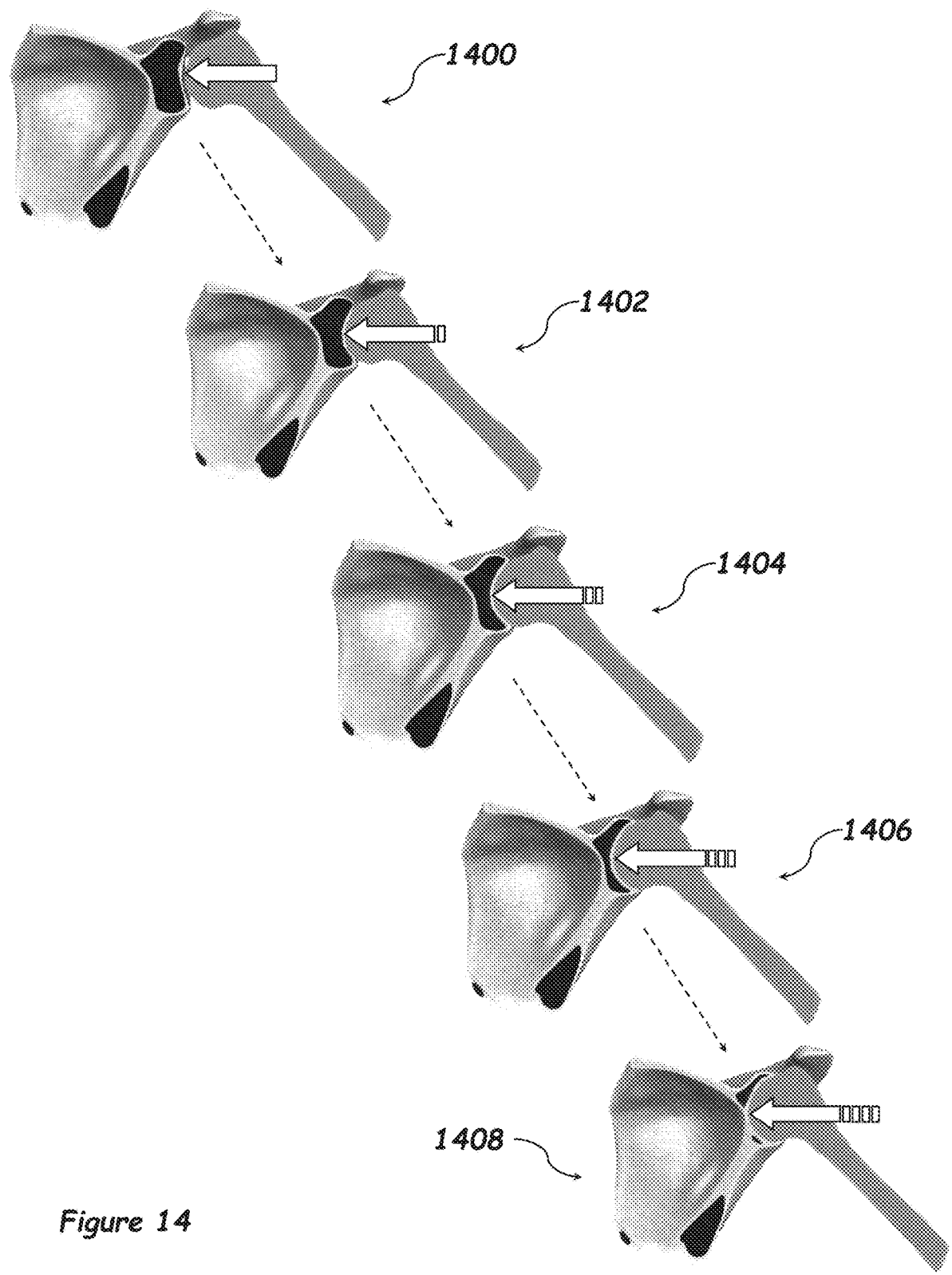
FIG. 14 is a sequence of images showing how the humerus can indent the scapula.

FIG. 14 illustrates the progression of the humerus being indented into the glenoid, where 1400 shows the humerus not indenting the glenoid, 1402 shows the humerus indenting the glenoid a distance $\beta_1$ from the position in 1400, 1404 shows the humerus indenting the glenoid a distance $\beta_2$ from the position in 1400, 1406 shows the humerus indenting the glenoid a distance $\beta_3$ from the position in 1400 and 1408 shows the humerus indenting the glenoid a distance $\beta_n$ from the position in 1400.

Figure 15:
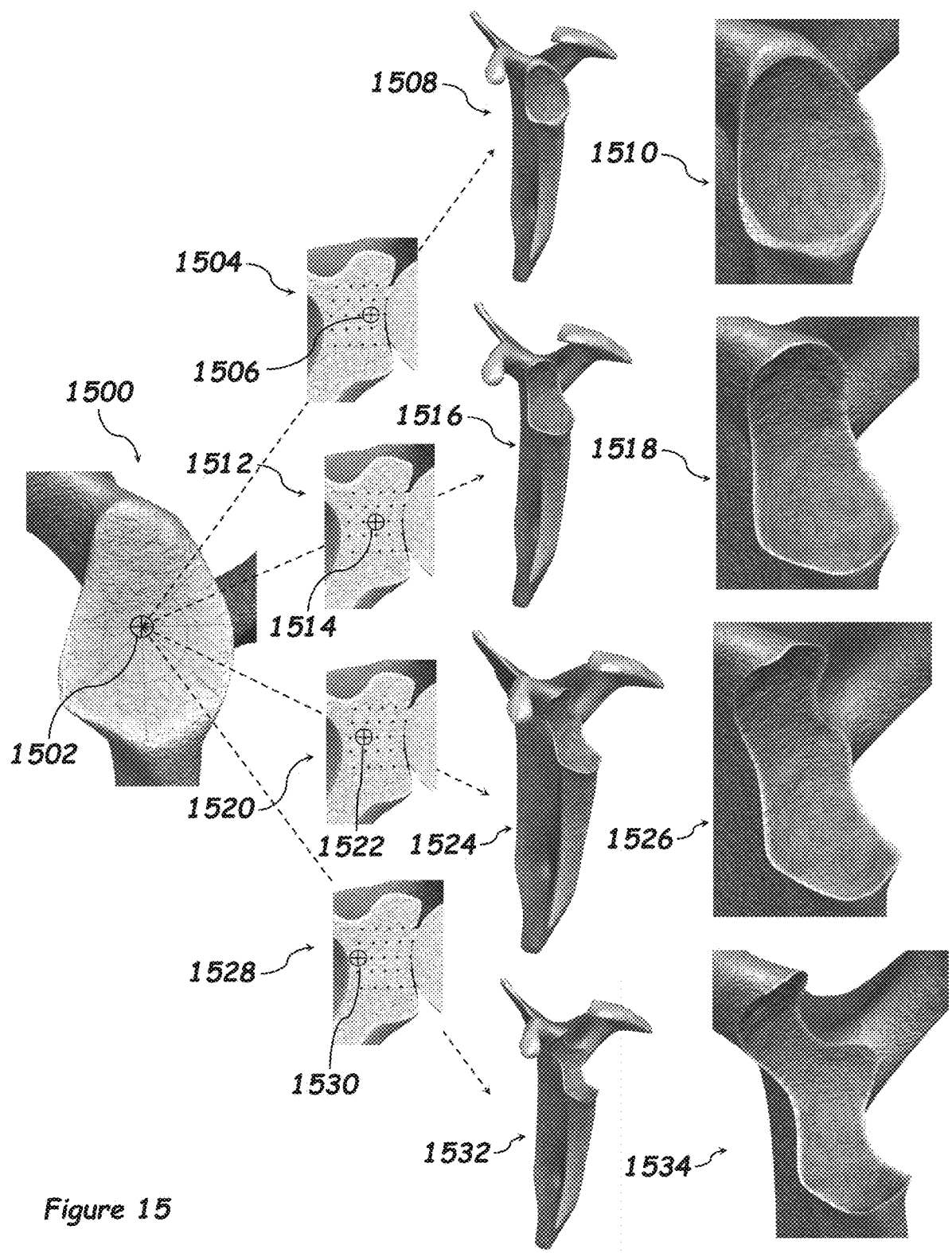
FIG. 15 is a sequence of images showing the central placement of the indent and how the indent can be visualized on the glenoid.

FIG. 15 illustrates how the defect created by indenting the humerus into the glenoid changes in relation to where and how deep the humerus is into the glenoid. The lateral view of the glenoid 1500 shows the central position on the glenoid 1502. The cross-section 1504 of the glenoid shows the first depth 1506 along the central position of the glenoid 1502. This position of the humerus into the glenoid creates a defect that can be seen in 1508 and a closeup of this defect in 1510. The cross-section 1512 of the glenoid shows the second depth 1514 along the central position of the glenoid 1502. This position of the humerus into the glenoid creates a defect that can be seen in 1516 and a closeup of this defect in 1518. The cross-section 1520 of the glenoid shows the third depth 1522 along the central position of the glenoid 1502. This position of the humerus into the glenoid creates a defect that can be seen in 1524 and a closeup of this defect in 1526. The cross-section 1528 of the glenoid shows the fourth depth 1530 along the central position of the glenoid 1502. This position of the humerus into the glenoid creates a defect that can be seen in 1532 and a closeup of this defect in 1534.

Figure 16:
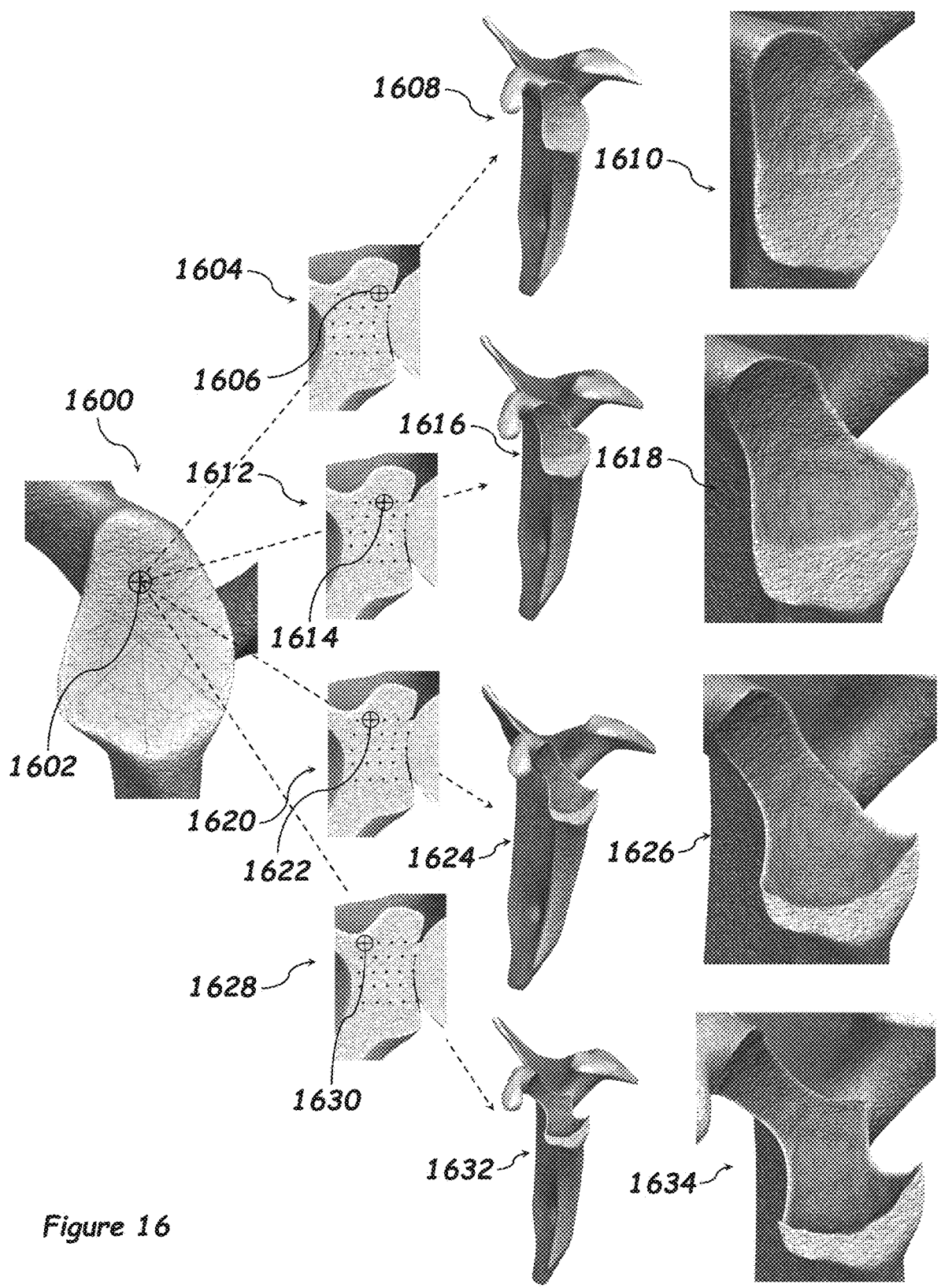
FIG. 16 is a sequence of images showing the superior placement of the indent and how the indent can be visualized on the glenoid.

FIG. 16 illustrates how the defect created by indenting the humerus into the glenoid changes in relation to where and how deep the humerus is into the glenoid. The lateral view of the glenoid 1600 shows the superior position on the glenoid 1602. The cross-section 1604 of the glenoid shows the first depth 1606 along the superior position of the glenoid 1602. This position of the humerus into the glenoid creates a defect that can be seen in 1608 and a closeup of this defect in 1610. The cross-section 1612 of the glenoid shows the second depth 1614 along the superior position of the glenoid 1602. This position of the humerus into the glenoid creates a defect that can be seen in 1616 and a closeup of this defect in 1618. The cross-section 1620 of the glenoid shows the third depth 1622 along the superior position of the glenoid 1602. This position of the humerus into the glenoid creates a defect that can be seen in 1624 and a closeup of this defect in 1626. The cross-section 1628 of the glenoid shows the fourth depth 1630 along the superior position of the glenoid 1602. This position of the humerus into the glenoid creates a defect that can be seen in 1632 and a closeup of this defect in 1634.

Figure 17:
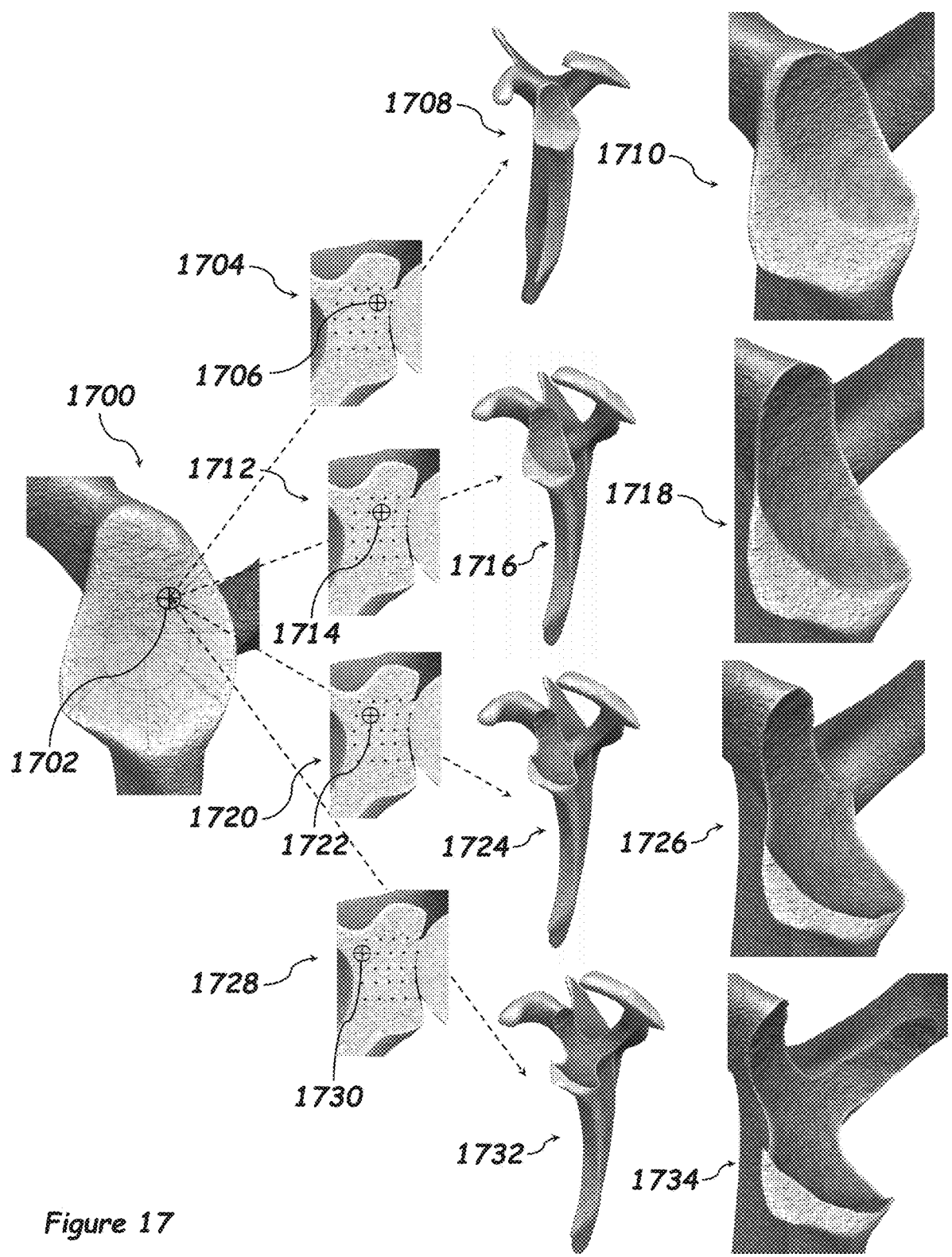
FIG. 17 is a sequence of images showing the superior-posterior placement of the indent and how the indent can be visualized on the glenoid.

FIG. 17 illustrates how the defect created by indenting the humerus into the glenoid changes in relation to where and how deep the humerus is into the glenoid. The lateral view of the glenoid 1700 shows the superior-posterior position on the glenoid 1702. The cross-section 1704 of the glenoid shows the first depth 1706 along the superior-posterior position of the glenoid 1702. This position of the humerus into the glenoid creates a defect that can be seen in 1708 and a closeup of this defect in 1710. The cross-section 1712 of the glenoid shows the second depth 1714 along the superior-posterior position of the glenoid 1702. This position of the humerus into the glenoid creates a defect that can be seen in 1716 and a closeup of this defect in 1718. The cross-section 1720 of the glenoid shows the third depth 1722 along the superior-posterior position of the glenoid 1702. This position of the humerus into the glenoid creates a defect that can be seen in 1724 and a closeup of this defect in 1726. The cross-section 1728 of the glenoid shows the fourth depth 1730 along the superior-posterior position of the glenoid 1702. This position of the humerus into the glenoid creates a defect that can be seen in 1732 and a closeup of this defect in 1734.

Figure 18:
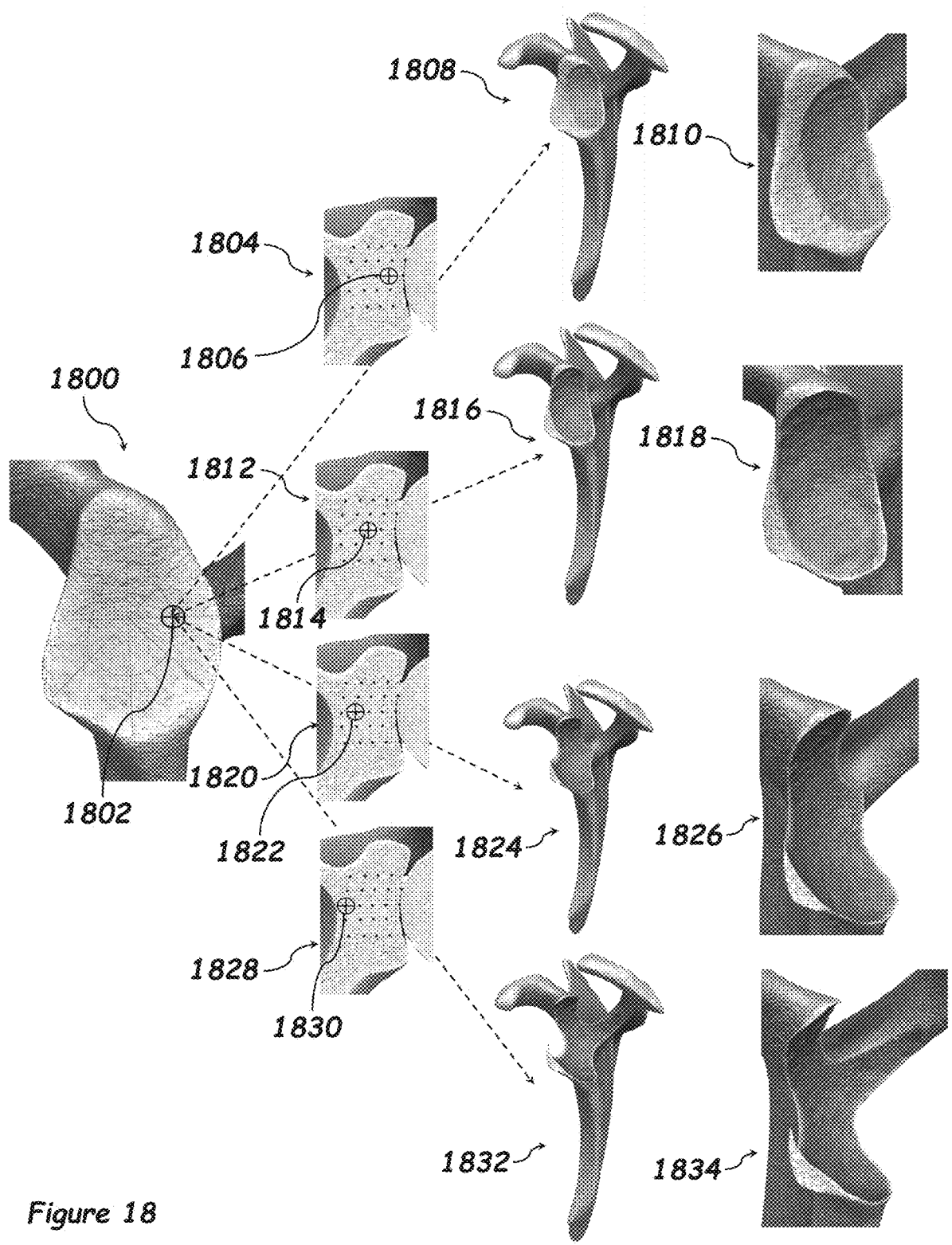
FIG. 18 is a sequence of images showing the posterior placement of the indent and how the indent can be visualized on the glenoid.

FIG. 18 illustrates how the defect created by indenting the humerus into the glenoid changes in relation to where and how deep the humerus is into the glenoid. The lateral view of the glenoid 1800 shows the posterior position on the glenoid 1802. The cross-section 1804 of the glenoid shows the first depth 1806 along the posterior position of the glenoid 1802. This position of the humerus into the glenoid creates a defect that can be seen in 1808 and a closeup of this defect in 1810. The cross-section 1812 of the glenoid shows the second depth 1814 along the posterior position of the glenoid 1802. This position of the humerus into the glenoid creates a defect that can be seen in 1816 and a closeup of this defect in 1818. The cross-section 1820 of the glenoid shows the third depth 1822 along the posterior position of the glenoid 1802. This position of the humerus into the glenoid creates a defect that can be seen in 1824 and a closeup of this defect in 1826. The cross-section 1828 of the glenoid shows the fourth depth 1830 along the posterior position of the glenoid 1802. This position of the humerus into the glenoid creates a defect that can be seen in 1832 and a closeup of this defect in 1834.

Figure 19:
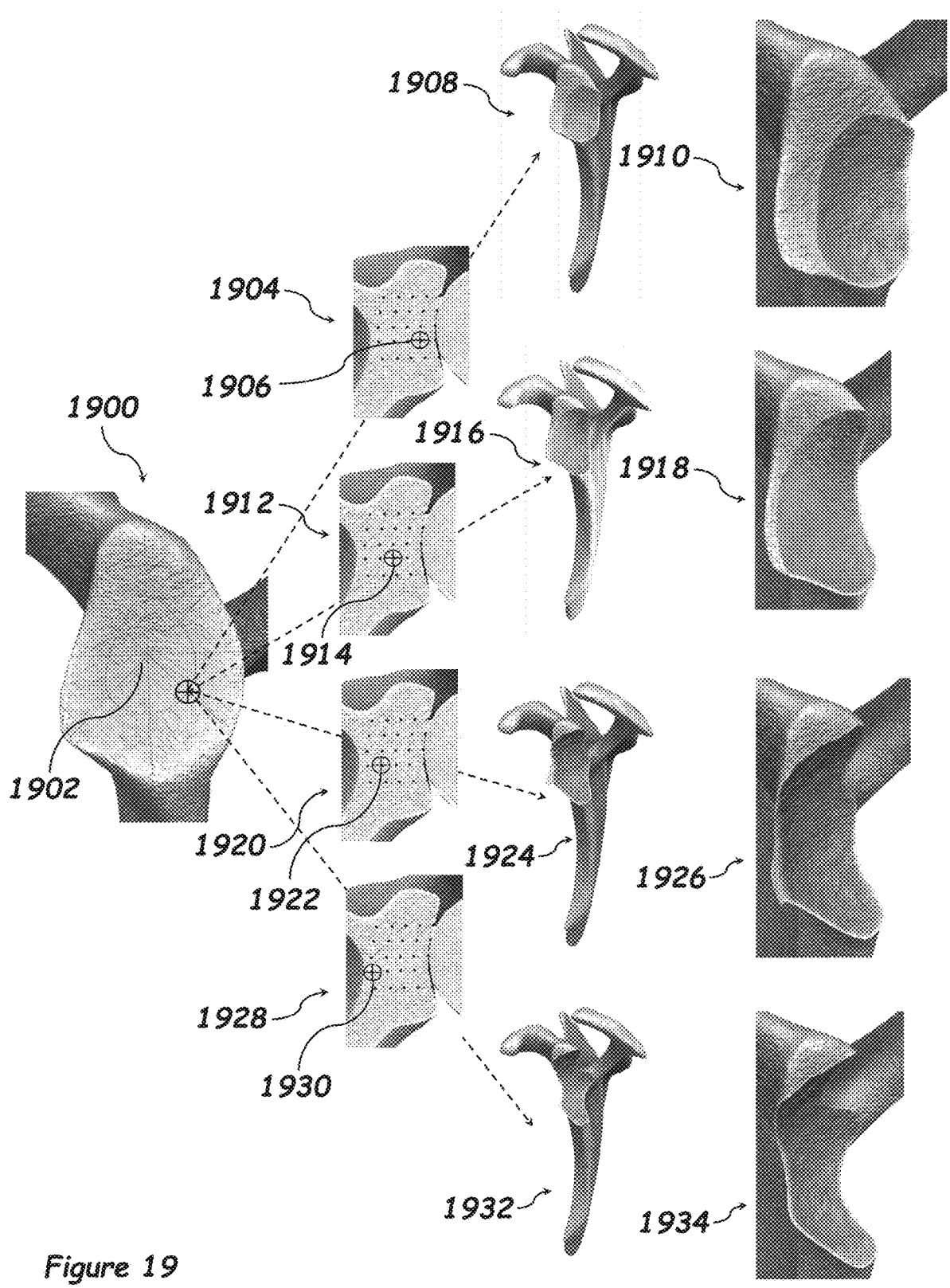
FIG. 19 is a sequence of images showing the inferior-posterior placement of the indent and how the indent can be visualized on the glenoid.

FIG. 19 illustrates how the defect created by indenting the humerus into the glenoid changes in relation to where and how deep the humerus is into the glenoid. The lateral view of the glenoid 1900 shows the inferior-posterior position on the glenoid 1902. The cross-section 1904 of the glenoid shows the first depth 1906 along the inferior-posterior position of the glenoid 1902. This position of the humerus into the glenoid creates a defect that can be seen in 1908 and a closeup of this defect in 1910. The cross-section 1912 of the glenoid shows the second depth 1914 along the inferior-posterior position of the glenoid 1902. This position of the humerus into the glenoid creates a defect that can be seen in 1916 and a closeup of this defect in 1918. The cross-section 1920 of the glenoid shows the third depth 1922 along the inferior-posterior position of the glenoid 1902. This position of the humerus into the glenoid creates a defect that can be seen in 1924 and a closeup of this defect in 1926. The cross-section 1928 of the glenoid shows the fourth depth 1930 along the inferior-posterior position of the glenoid 1902. This position of the humerus into the glenoid creates a defect that can be seen in 1932 and a closeup of this defect in 1934.

Figure 20:
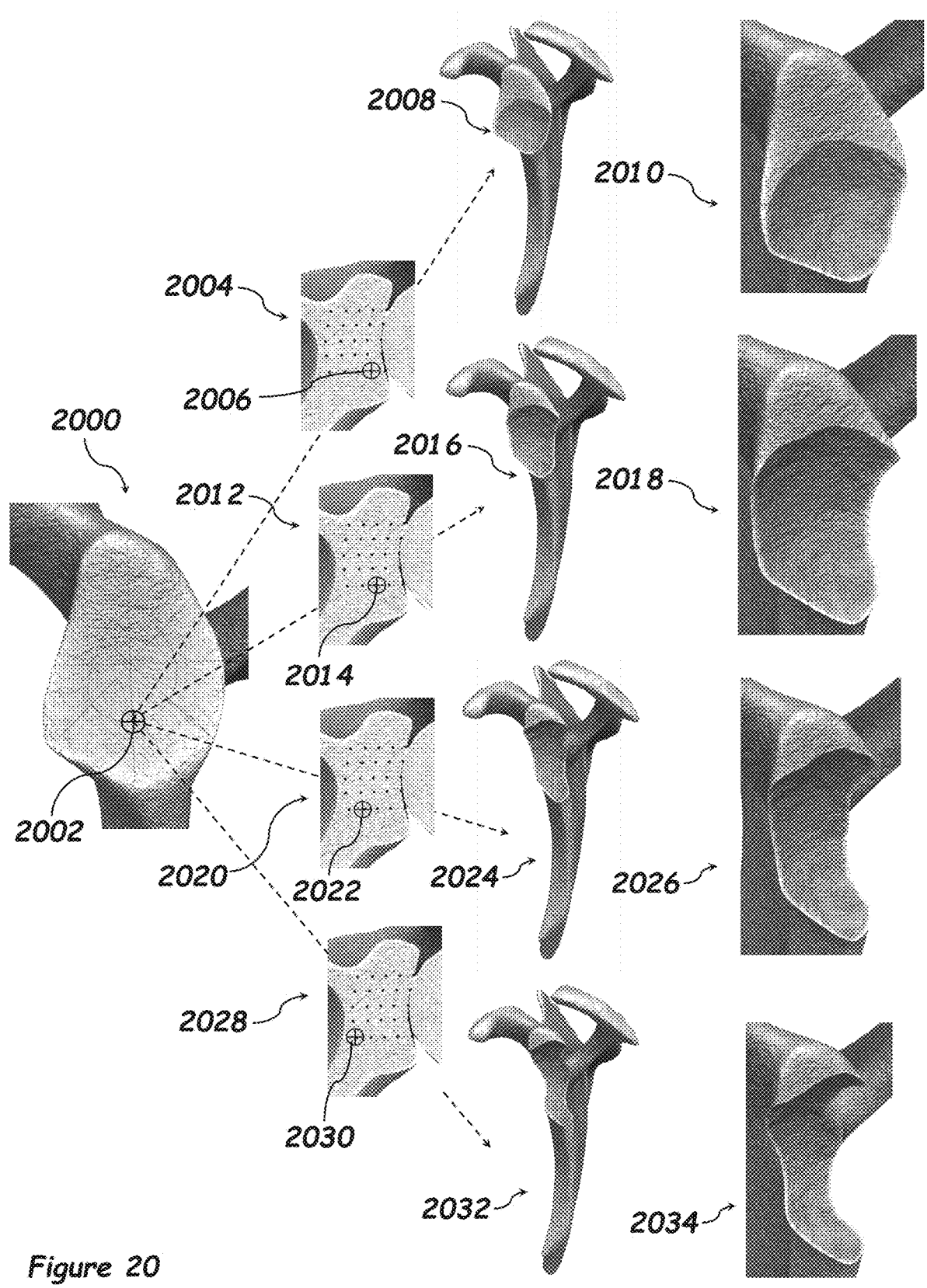
FIG. 20 is a sequence of images showing the inferior placement of the indent and how the indent can be visualized on the glenoid.

FIG. 20 illustrates how the defect created by indenting the humerus into the glenoid changes in relation to where and how deep the humerus is into the glenoid. The lateral view of the glenoid 2000 shows the inferior position on the glenoid 2002. The cross-section 2004 of the glenoid shows the first depth 2006 along the inferior position of the glenoid 2002. This position of the humerus into the glenoid creates a defect that can be seen in 2008 and a closeup of this defect in 2010. The cross-section 2012 of the glenoid shows the second depth 2014 along the inferior position of the glenoid 2002. This position of the humerus into the glenoid creates a defect that can be seen in 2016 and a closeup of this defect in 2018. The cross-section 2020 of the glenoid shows the third depth 2022 along the inferior position of the glenoid 2002. This position of the humerus into the glenoid creates a defect that can be seen in 2024 and a closeup of this defect in 2026. The cross-section 2028 of the glenoid shows the fourth depth 2030 along the inferior position of the glenoid 2002. This position of the humerus into the glenoid creates a defect that can be seen in 2032 and a closeup of this defect in 2034.

Figure 21:
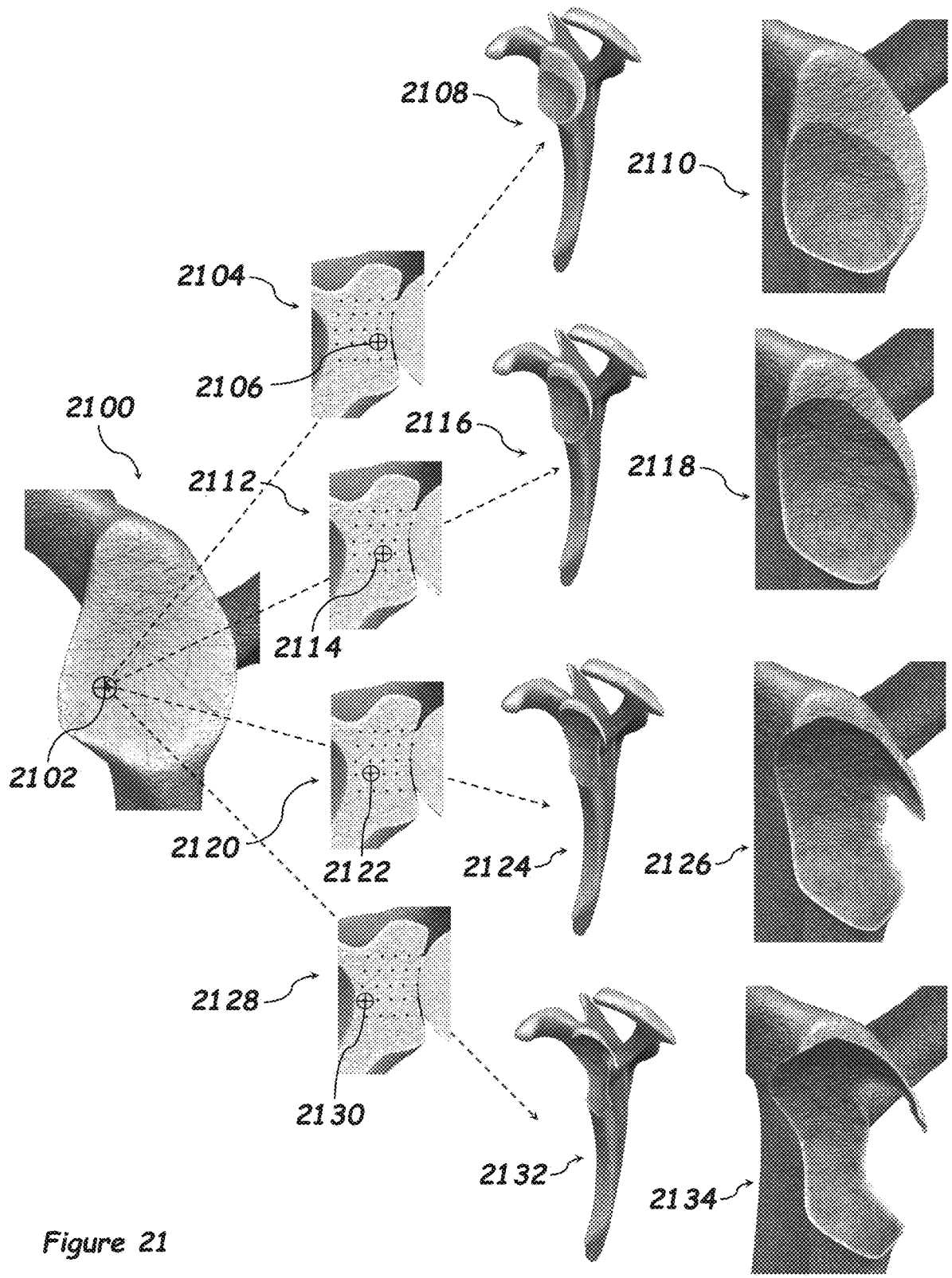
FIG. 21 is a sequence of images showing the inferior-anterior placement of the indent and how the indent can be visualized on the glenoid.

FIG. 21 illustrates how the defect created by indenting the humerus into the glenoid changes in relation to where and how deep the humerus is into the glenoid. The lateral view of the glenoid 2100 shows the inferior-anterior position on the glenoid 2102. The cross-section 2104 of the glenoid shows the first depth 2106 along the inferior-anterior position of the glenoid 2102. This position of the humerus into the glenoid creates a defect that can be seen in 2108 and a closeup of this defect in 2110. The cross-section 2112 of the glenoid shows the second depth 2114 along the inferior-anterior position of the glenoid 2102. This position of the humerus into the glenoid creates a defect that can be seen in 2116 and a closeup of this defect in 2118. The cross-section 2120 of the glenoid shows the third depth 2122 along the inferior-anterior position of the glenoid 2102. This position of the humerus into the glenoid creates a defect that can be seen in 2124 and a closeup of this defect in 2126. The cross-section 2128 of the glenoid shows the fourth depth 2130 along the inferior-anterior position of the glenoid 2102. This position of the humerus into the glenoid creates a defect that can be seen in 2132 and a closeup of this defect in 2134.

Figure 22:
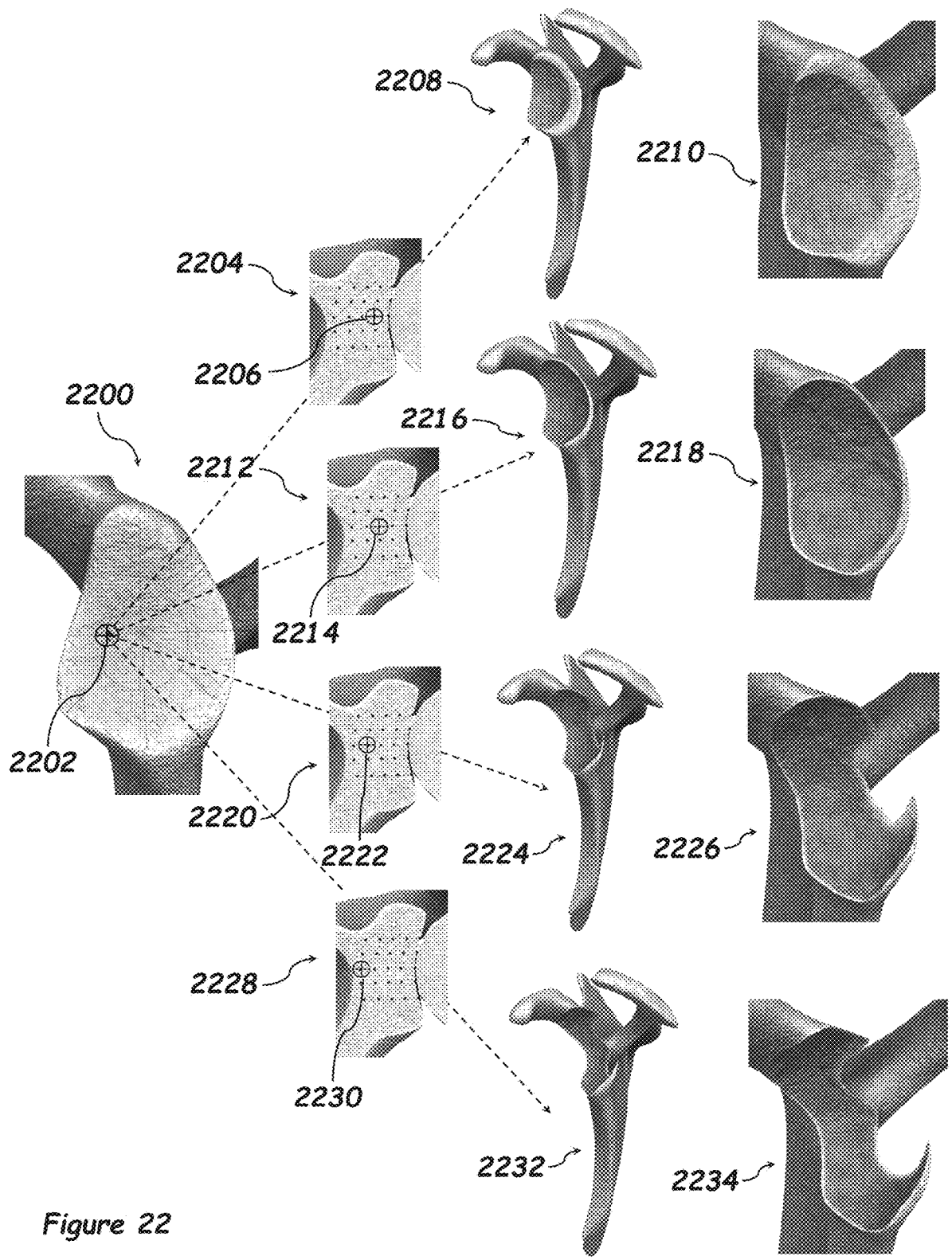
FIG. 22 is a sequence of images showing the anterior placement of the indent and how the indent can be visualized on the glenoid.

FIG. 22 illustrates how the defect created by indenting the humerus into the glenoid changes in relation to where and how deep the humerus is into the glenoid. The lateral view of the glenoid 2200 shows the anterior position on the glenoid 2202. The cross-section 2204 of the glenoid shows the first depth 2206 along the anterior position of the glenoid 2202. This position of the humerus into the glenoid creates a defect that can be seen in 2208 and a closeup of this defect in 2210. The cross-section 2212 of the glenoid shows the second depth 2214 along the anterior position of the glenoid 2202. This position of the humerus into the glenoid creates a defect that can be seen in 2216 and a closeup of this defect in 2218. The cross-section 2220 of the glenoid shows the third depth 2222 along the anterior position of the glenoid 2202. This position of the humerus into the glenoid creates a defect that can be seen in 2224 and a closeup of this defect in 2226. The cross-section 2228 of the glenoid shows the fourth depth 2230 along the anterior position of the glenoid 2202. This position of the humerus into the glenoid creates a defect that can be seen in 2232 and a closeup of this defect in 2234.

Figure 23:
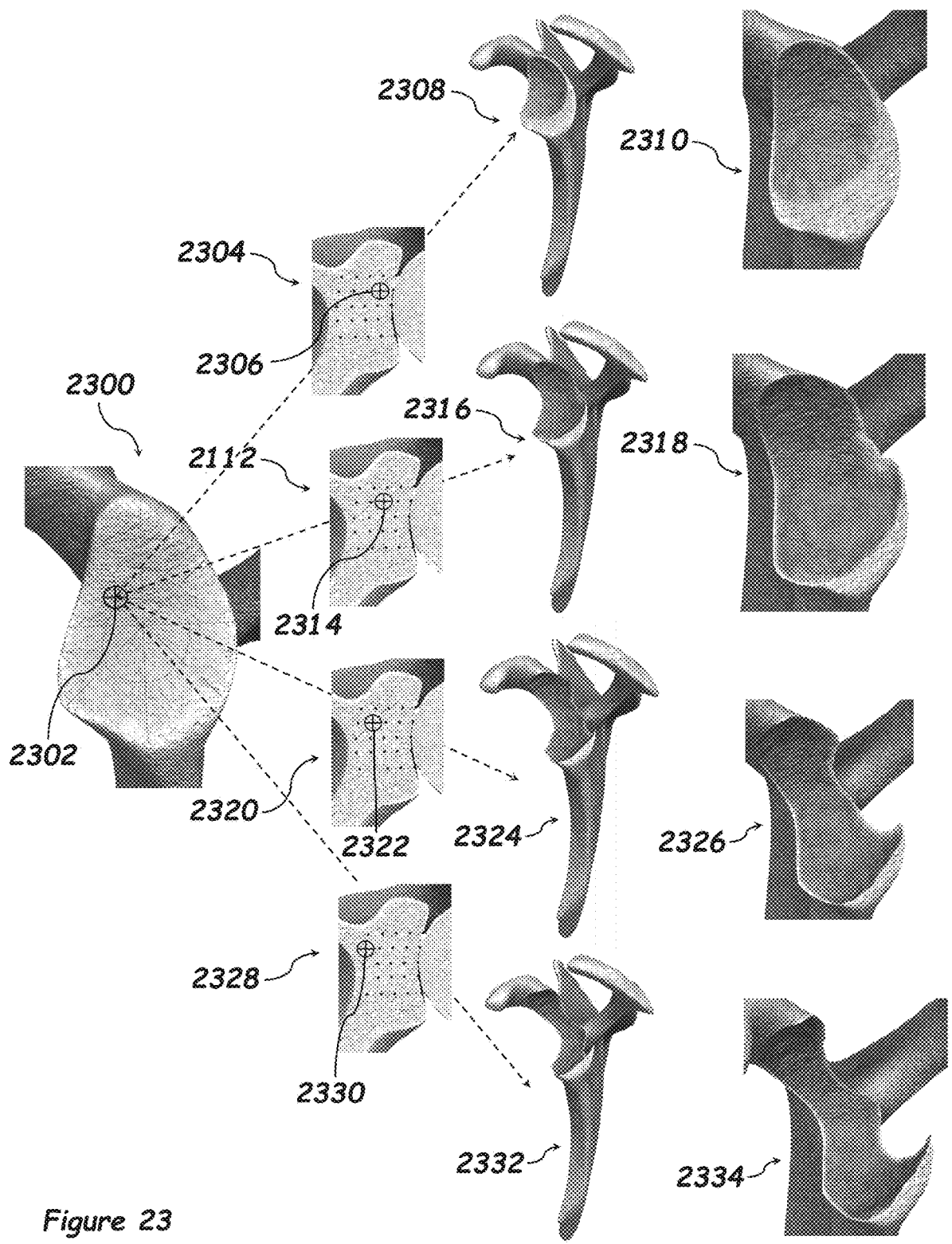
FIG. 23 is a sequence of images showing the superior-anterior placement of the indent and how the indent can be visualized on the glenoid.

FIG. 23 illustrates how the defect created by indenting the humerus into the glenoid changes in relation to where and how deep the humerus is into the glenoid. The lateral view of the glenoid 2300 shows the superior-anterior position on the glenoid 2302. The cross-section 2304 of the glenoid shows the first depth 2306 along the superior-anterior position of the glenoid 2302. This position of the humerus into the glenoid creates a defect that can be seen in 2308 and a closeup of this defect in 2310. The cross-section 2312 of the glenoid shows the second depth 2314 along the superior-anterior position of the glenoid 2302. This position of the humerus into the glenoid creates a defect that can be seen in 2316 and a closeup of this defect in 2318. The cross-section 2320 of the glenoid shows the third depth 2322 along the superior-anterior position of the glenoid 2302. This position of the humerus into the glenoid creates a defect that can be seen in 2324 and a closeup of this defect in 2326. The cross-section 2328 of the glenoid shows the fourth depth 2330 along the superior-anterior position of the glenoid 2302. This position of the humerus into the glenoid creates a defect that can be seen in 2332 and a closeup of this defect in 2334.

Figure 24:
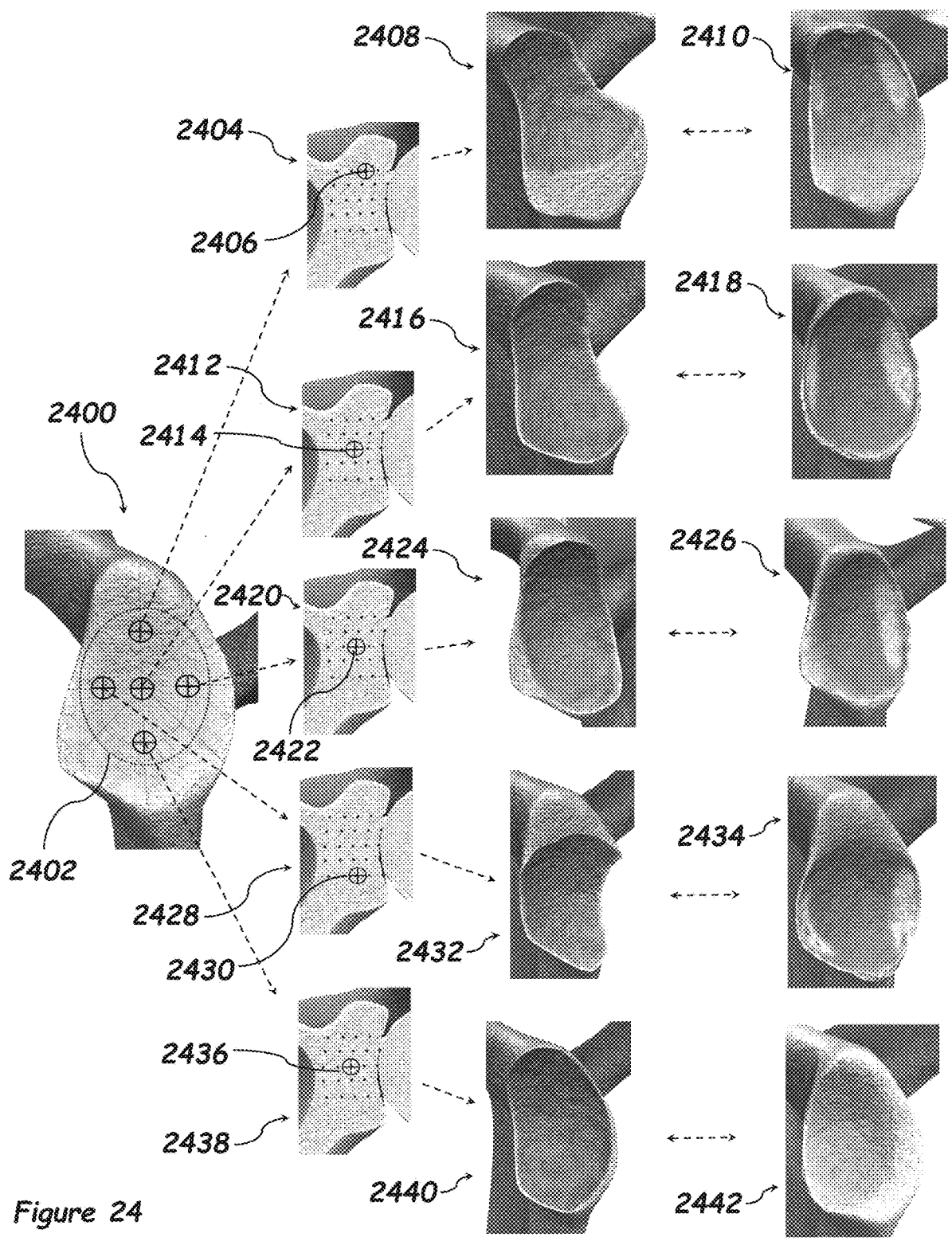
FIG. 24 is a sequence of images showing methods to create the desired defect on a bone.

FIG. 24 illustrates the possible methods for creating a bone defect. The lateral view of the glenoid 2400 shows the different positions on the glenoid 2402 that are being illustrated. The cross-section 2404 of the glenoid shows the depth 2406 along the superior position of the glenoid 2404. This position of the humerus into the glenoid creates a defect that can be seen in 2408 as a subtractive method and 2410 as an adaptive method. The cross-section 2412 of the glenoid shows the depth 2414 along the central position of the glenoid 2402. This position of the humerus into the glenoid creates a defect that can be seen in 2416 as a subtractive method and 2418 as an adaptive method. The cross-section 2420 of the glenoid shows the depth 2422 along the posterior position of the glenoid 2402. This position of the humerus into the glenoid creates a defect that can be seen in 2424 as a subtractive method and 2426 as an adaptive method. The cross-section 2428 of the glenoid shows the depth 2430 along the inferior position of the glenoid 2402. This position of the humerus into the glenoid creates a defect that can be seen in 2432 as a subtractive method and 2434 as an adaptive method. The cross-section 2438 of the glenoid shows the depth 2436 along the anterior position of the glenoid 2402. This position of the humerus into the glenoid creates a defect that can be seen in 2440 as a subtractive method and 2442 as an adaptive method. FIGS. 2408, 2416, 2424, 2432 and 2440 illustrate a subtractive method where the intersection of one bone with another is subtracted creating the desired defect. FIGS. 2410, 2418, 2426, 2434 and 2442 illustrate an adaptive method where one bone is collided with another bone to create the desired defect.

General Interpretive Principles for the Present Disclosure

Various aspects of the novel systems, apparatuses, and methods are described more fully above with reference to the accompanying drawings. The teachings may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the novel systems, apparatuses, and methods disclosed herein, whether implemented independently of or combined with any other aspect of the disclosure. For example, a system or an apparatus may be implemented, or a method may be practiced using any one or more of the aspects set forth herein. In addition, the scope of the disclosure is intended to cover such a system, apparatus or method which is practiced using other structure, functionality, or structure and functionality in addition to or other than the various aspects of the disclosure set forth herein. It should be understood that any aspect disclosed herein may be set forth in one or more elements of a claim. Although some benefits and advantages of the preferred aspects are mentioned, the scope of the disclosure is not intended to be limited to particular benefits, uses, or objectives. The detailed description and drawings are merely illustrative of the disclosure rather than limiting, the scope of the disclosure being defined by the appended claims and equivalents thereof.

With respect to the use of plural vs. singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that terms used herein, and especially in the appended claims (e.g., bodies of the appended claims) are intended as "open" terms unless specifically indicated otherwise (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

In those instances where a convention analogous to "at least one of A, B, and C" is used, such a construction would include systems that have A alone, B alone, C alone, A and B together without C, A and C together without B, B and C together without A, as well as A, B, and C together. It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include A without B, B without A, as well as A and B together."

The word "exemplary" is used exclusively herein to mean "serving as an example, instance, or illustration." Any implementation described herein as "exemplary" is not necessarily to be construed as preferred or advantageous over other implementations.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

What is claimed is:

1. A method of pre-operative planning for a surgical procedure to be performed on a physiologically defective joint of a patient, the method comprising:
   generating or receiving, with a computerized pre-operative surgical planning system, a computer model of the patient's physiologically defective joint comprising at least a first bone and a second bone;
   receiving, with the computerized pre-operative surgical planning system, a plurality of pre-diseased and physiologically healthy patient bone models corresponding to the patient's physiologically defective joint, wherein each of the plurality of pre-diseased and physiologically healthy patient bone models comprises the first bone in a respective one of a plurality of different positions and/or orientations with respect to the second bone;
   applying, by the computerized pre-operative surgical planning system, disorder progression parameters to each of the pre-diseased and physiologically healthy patient bone models to, thereby, artificially generate a respective plurality of computer models of bony defects corresponding to the patient's physiologically defective joint;
   selecting, by the computerized pre-operative surgical planning system, the pre-diseased and physiologically healthy patient, bone model corresponding to the artificially generated computer model of bony defects corresponding to the patient's physiologically defective joint that most closely matches the computer model of the patient's physiologically defective joint;
   based at least in part on the selected pre-diseased and physiologically healthy patient bone model, generating, by the computerized pre-operative surgical planning system, a computer model approximating the patient's joint prior to the patient's joint becoming defective; and
   displaying a visual representation of the computer model approximating the patient's joint prior to the patient's joint becoming defective.

2. The method of claim 1, further comprising:
   generating, with the computerized pre-operative surgical planning system, at least one candidate element for a pre-operative surgical plan based at least in part on the generated computer model approximating the patient's joint prior to the patient's joint becoming defective; and
   displaying a visual representation of the generated candidate element of the pre-operative surgical procedure plan.

3. The method of claim 2, wherein the generated candidate element of the pre-operative surgical plan comprises a selection of an implant to be affixed to the patient's physiologically defective join during the surgical procedure.

4. The method of claim 3, further comprising identifying a defect type exhibited by the patient's physiologically defective joint.

5. The method of claim 1, wherein the computer model of the patient's physiologically defective joint is based at least in part on information acquired with one or more imaging modalities.

6. The method of claim 1, wherein the generating of the computer model approximating the patient's joint prior to the patient's join becoming defective is performed using a machine learning classifier.

7. The method of claim 1, further comprising identifying a defect type exhibited by the patient's physiologically defective joint.

* * * * *